(12) United States Patent
Sawada et al.

(10) Patent No.: US 9,671,298 B2
(45) Date of Patent: Jun. 6, 2017

(54) FORCE SENSOR AND ROBOT HAVING FORCE SENSOR

(71) Applicants: KABUSHIKI KAISHA YASKAWA DENKI, Kitakyushu-shi (JP); KYUSHU UNIVERSITY, NATIONAL UNIVERSITY CORPORATION, Fukuoka-shi (JP)

(72) Inventors: Renshi Sawada, Fukuoka (JP); Toshihiro Takeshita, Fukuoka (JP); Takuma Iwasaki, Fukuoka (JP); Yuji Arinaga, Fukuoka (JP)

(73) Assignees: KABUSHIKI KAISHA YASKAWA DENKI, Kitakyushu-Shi (JP); KYUSHU UNIVERSITY, NATIONAL UNIVERSITY CORPORATION, Fukuoka-Shi (JP)

( * ) Notice: Subject to any disclaimer, the term of this patent is extended or adjusted under 35 U.S.C. 154(b) by 115 days.

(21) Appl. No.: 14/640,022

(22) Filed: Mar. 6, 2015

(65) Prior Publication Data

US 2015/0177082 A1 Jun. 25, 2015

Related U.S. Application Data

(63) Continuation of application No. PCT/JP2013/069067, filed on Jul. 11, 2013.

(30) Foreign Application Priority Data

Sep. 21, 2012 (JP) .................................. 2012-208969

(51) Int. Cl.
*G01L 1/24* (2006.01)
*A61B 5/00* (2006.01)
(Continued)

(52) U.S. Cl.
CPC .............. *G01L 1/241* (2013.01); *B25J 9/1697* (2013.01); *G01B 11/16* (2013.01); *G01L 1/044* (2013.01);
(Continued)

(58) Field of Classification Search
CPC ....... G01B 11/16; G01L 1/24; G01L 1/241; G01L 5/166; G01L 5/0047
See application file for complete search history.

(56) References Cited

U.S. PATENT DOCUMENTS 5,844,146 A 12/1998 Murray et al.
6,067,862 A 5/2000 Murray et al.
(Continued)

FOREIGN PATENT DOCUMENTS

JP 60-31639 U 3/1985
JP 9-509497 9/1997
(Continued)

OTHER PUBLICATIONS

International Search Report for corresponding International Application No. PCT/JP2013/069067, Sep. 17, 2013.
(Continued)

*Primary Examiner* — Kara E Geisel
*Assistant Examiner* — Violeta A Prieto
(74) *Attorney, Agent, or Firm* — Mori & Ward, LLP

(57) ABSTRACT

A force sensor according to embodiments includes a light-emitting unit, a pair of first light detectors, a reflector, and a first frame. The light-emitting unit emits diffuse light. The first light detectors are arranged in a first direction with the light-emitting unit interposed therebetween. The reflector is arranged to face the light-emitting unit on an optical axis of the light-emitting unit and reflects the diffuse light emitted from the light-emitting unit toward the first light detectors. The first frame is deformed in the first direction so that a (Continued)

reflection range of the diffuse light reflected by the reflector is displaced in the first direction.

11 Claims, 17 Drawing Sheets

(51) Int. Cl.
    *B25J 9/16*         (2006.01)
    *G01B 11/16*    (2006.01)
    *G01L 5/00*       (2006.01)
    *G01L 5/16*       (2006.01)
    *G01L 5/22*       (2006.01)
    *G01L 1/04*       (2006.01)

(52) U.S. Cl.
    CPC .............. *G01L 1/24* (2013.01); *G01L 5/0047* (2013.01); *G01L 5/166* (2013.01); *G01L 5/221* (2013.01); *A61B 5/445* (2013.01); *Y10S 901/47* (2013.01)

(56) References Cited

U.S. PATENT DOCUMENTS

| | | | |
|---|---|---|---|
| 7,090,647 B2 | 8/2006 | Mimura et al. | |
| 7,652,767 B2* | 1/2010 | Harsh | G01J 3/02 356/445 |
| 8,749,522 B2* | 6/2014 | Dietzel | G01L 1/241 345/175 |
| 2005/0148904 A1* | 7/2005 | Mimura | A61B 5/1126 600/587 |
| 2008/0094632 A1* | 4/2008 | Harsh | G01J 3/02 356/436 |
| 2010/0253650 A1 | 10/2010 | Dietzel et al. | |

FOREIGN PATENT DOCUMENTS

| | | |
|---|---|---|
| JP | 11-190744 | 7/1999 |
| JP | 2003-042861 | 2/2003 |
| JP | 2005-257412 | 9/2005 |
| JP | 2010-539474 | 12/2010 |
| WO | WO 03/079898 | 10/2003 |

OTHER PUBLICATIONS

Written Opinion for corresponding International Application No. PCT/JP2013/069067, Sep. 17, 2013.

English translation of the Written Opinion for corresponding International Application No. PCT/JP2013/069067, Sep. 17, 2013.

Japanese Office Action for corresponding JP Application No. 2014-536640, Sep. 1, 2015.

\* cited by examiner

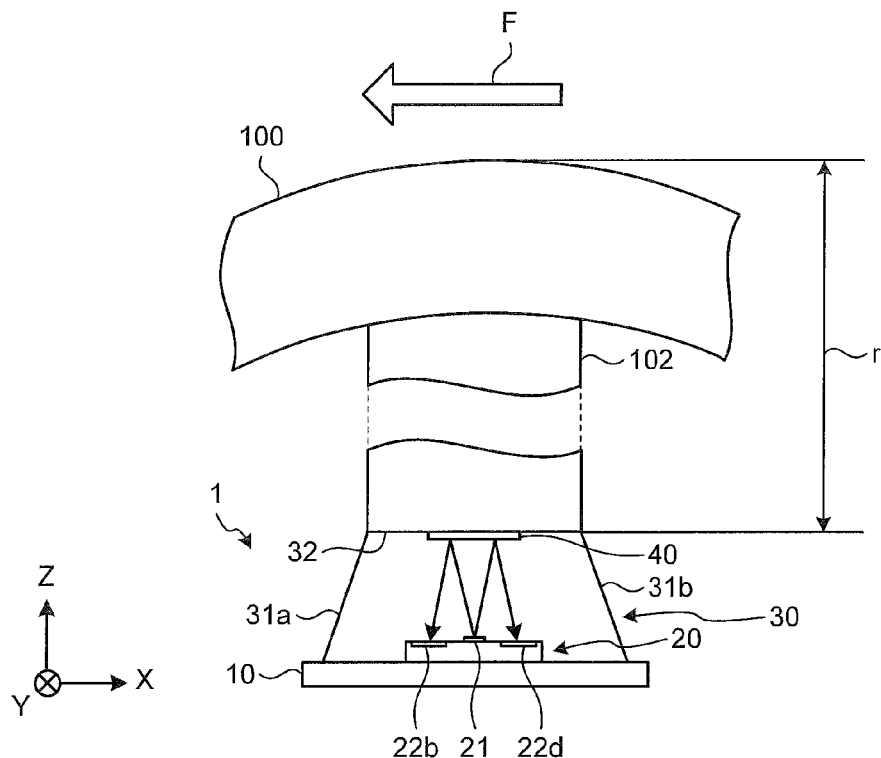
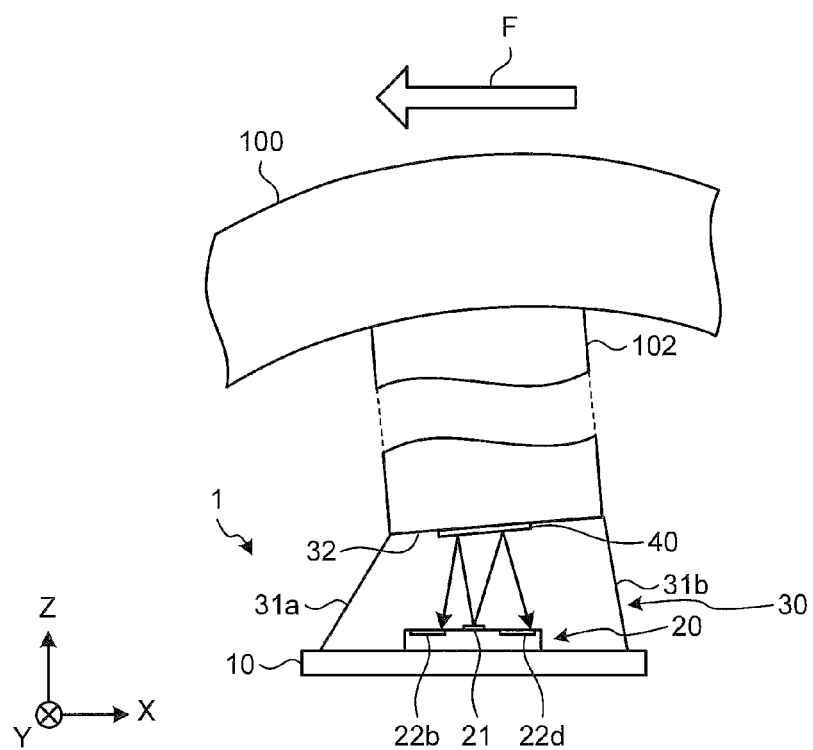

FIG.10

|  | Material | Young modulus | Corner Angle $\theta$ | |
|---|---|---|---|---|
|  |  |  | left | right |
| (a) | Stainless (SUS304) | 197GPa | 105° | 110° |
| (b) |  |  | 115° | 120° |
| (c) | Copper (OFC) | 128GPa | 111° | 112° |
| (d) |  |  | 118° | 122° |

FORCE SENSOR AND ROBOT HAVING FORCE SENSOR

CROSS-REFERENCE TO RELATED APPLICATION

This application is a continuation of International Application No. PCT/JP2013/069067, filed on Jul. 11, 2013 which claims the benefit of priority from Japanese Patent Application No. 2012-208969, filed on Sep. 21, 2012, the entire contents of which are incorporated herein by reference.

FIELD

The embodiments discussed herein are directed to a force sensor and a robot having the force sensor.

BACKGROUND

Shearing force (friction) applied to a human body is one of the causes of a bedsore. For example, when a bed is inclined, shearing force occurs between a human body and the bed, thereby causing a bedsore in some cases.

In recent years, an attempt has been made to embed a force sensor for detecting shearing force in bedding such as an anti-bedsore mattress to detect the shearing force occurring between a human body and the bedding (e.g., see WO2003/079898).

The conventional technique described above, however, has a room for further improvement in that the shearing force can be detected with a simpler structure.

SUMMARY

A force sensor according to an aspect of embodiments includes a light-emitting unit, a pair of first light detectors, a reflector, and a first frame. The light-emitting unit emits diffuse light. The first light detectors are arranged in a first direction with the light-emitting unit interposed therebetween. The reflector is arranged to face the light-emitting unit on an optical axis of the light-emitting unit, and reflects the diffuse light emitted from the light-emitting unit toward the pair of first light detectors. The first frame is deformed in the first direction so that a reflection range of the diffuse light reflected by the reflector is displaced in the first direction.

BRIEF DESCRIPTION OF DRAWINGS

A more complete appreciation of the embodiments and many of the attendant advantages thereof will be readily obtained as the same becomes better understood by reference to the following detailed description when considered in connection with the accompanying drawings, wherein:

FIG. 9A is an explanatory view of a detection principle of torque by the force sensor according to the first embodiment;

FIG. 9B is another explanatory view of the detection principle of torque by the force sensor according to the first embodiment;

FIG. 10 is an explanatory view illustrating an example of experiment conditions on torque detection by the force sensor according to the first embodiment;

DESCRIPTION OF EMBODIMENTS

Hereinafter, a force sensor and a robot having the force sensor according to embodiments of the present disclosure will be explained in detail with reference to the accompanying drawings. In addition, the following embodiments are not intended to limit the present invention.

First Embodiment

Figure 1:
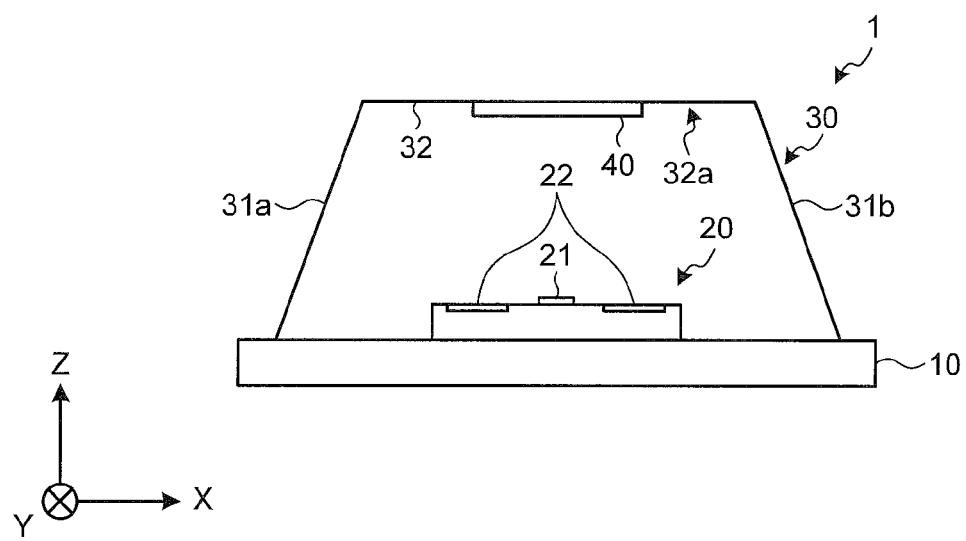
FIG. 1 is a schematic side view of a force sensor according to a first embodiment.

FIG. 1 is a schematic side view of a force sensor according to a first embodiment. In the following description, X, Y, and Z axes that are orthogonal to each other are set, and the positive direction of the Z axis is defined as the upper vertical direction, to clearly describe a positional relation.

As illustrated in FIG. 1, a force sensor 1 according to the first embodiment includes a base 10, a displacement sensor 20 provided on the base 10, and a first frame (hereinafter, described as a "variable frame 30") that is fixed to the base 10 and covers the displacement sensor 20. The force sensor 1 further includes a reflector (hereinafter, described as a "mirror 40") provided on a surface that faces the displacement sensor 20 of the variable frame 30. Herein, the reflector corresponds to means for reflecting diffuse light, and the first frame corresponds to means for displacing the reflection range of the diffuse light reflected by the means for reflecting.

The displacement sensor 20 includes a light-emitting unit 21 and a light detector 22. The light-emitting unit 21 emits diffuse light, specifically, diffuse laser light. As the light-emitting unit 21, a vertical cavity surface emitting laser (VCSEL) can be used, for example. The VCSEL is a surface emitting laser in which a resonator is made perpendicular to a semiconductor substrate. Herein, the light-emitting unit 21 corresponds to means for emitting diffuse light.

The light detector 22 detects diffuse laser light reflected by the mirror 40. As the light detector 22, a photo diode can be used, for example. The mirror 40 and the variable frame 30 may be integrally formed.

Figure 2:
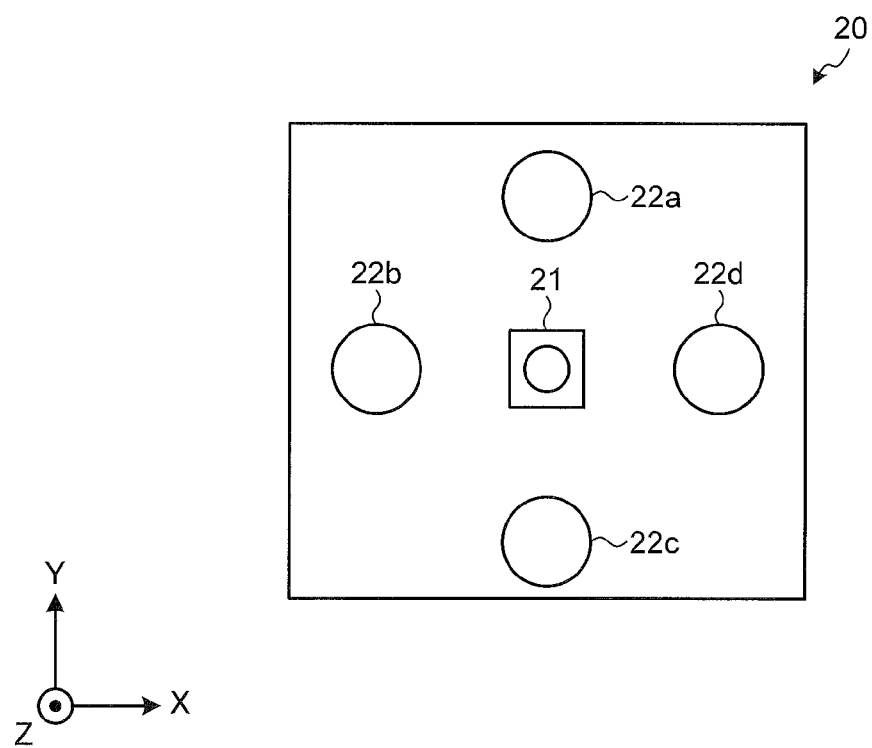
FIG. 2 is a schematic plan view of a displacement sensor.

The following describes the arrangement of the light-emitting unit 21 and the light detector 22 with reference to FIG. 2. FIG. 2 is a schematic plan view of the displacement sensor 20.

As illustrated in FIG. 2, the displacement sensor 20 includes the light-emitting unit 21 disposed at the center and light detectors 22a to 22d arranged in the four directions from the light-emitting unit 21. In the example illustrated in FIG. 2, the light detectors 22b and 22d are arranged along a first direction (in this case, in the positive direction of the X axis) in this order while the light detectors 22a and 22c are arranged along a second direction (in this case, in the positive direction of the Y axis) in this order. In the following description, the light detectors 22b and 22d are described as first light detectors 22b and 22d while the light detectors 22a and 22c are described as second light detectors 22a and 22c in some cases.

The displacement sensor 20 has a width of substantially 3.0 mm, a length of substantially 3.0 mm, and a thickness of substantially 1.6 mm, for example.

Figure 3A:
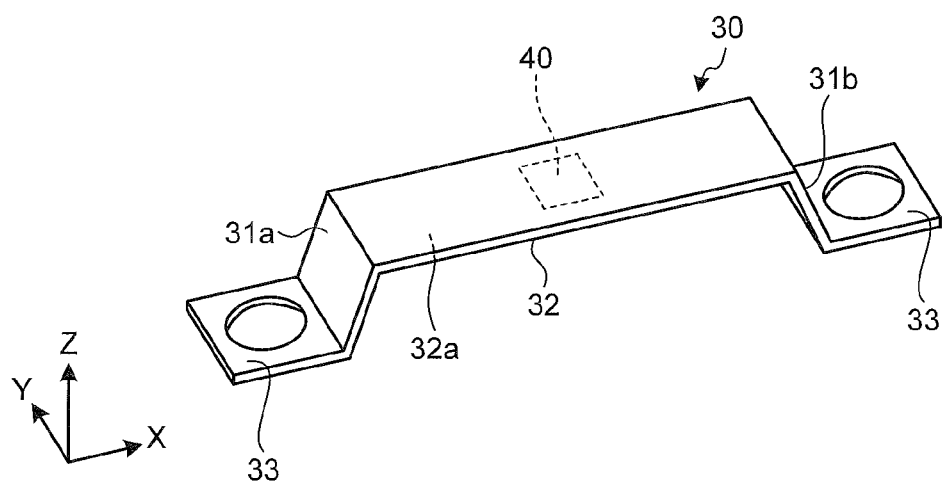
FIG. 3A is a schematic perspective view of a variable frame.
Figure 3B:
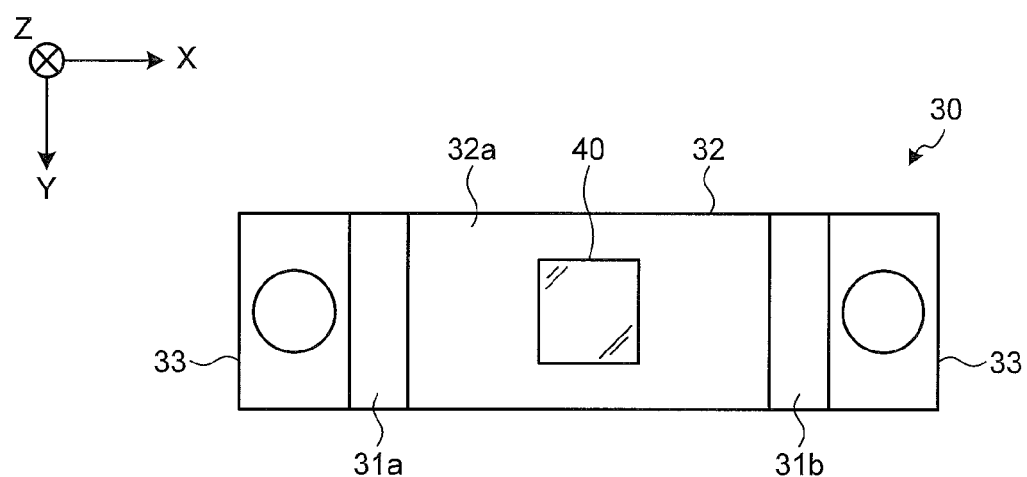
FIG. 3B is a schematic rear view of the variable frame.

The following describes the structures of the variable frame 30 and the mirror 40 with reference to FIGS. 1, 3A, and 3B. FIG. 3A is a schematic perspective view of the variable frame 30. FIG. 3B is a schematic rear view of the variable frame 30.

The variable frame 30 is a member that has an approximate trapezoidal shape in a side view and covers the displacement sensor 20, as illustrated in FIG. 1. Specifically, the variable frame 30 includes supports 31a and 31b and a ceiling 32. The supports 31a and 31b are inclined with respect to the vertical direction (Z-axis direction). The ceiling 32 is connected to the supports 31a and 31b at both ends thereof and is horizontally supported by the supports 31a and 31b. In the example illustrated in FIG. 1, the support 31a is inclined to the positive direction side in the X-axis direction with respect to the vertical direction while the support 31b is inclined to the negative direction side in the X-axis direction with respect to the vertical direction.

The variable frame 30 has a degree of freedom at the connecting portions of the respective supports 31a and 31b and the ceiling 32, that is, the corners of the variable frame 30. The variable frame 30 is thus configured to be deformed when a force is applied in the X-axis direction, resulting in the ceiling 32 being inclined.

The variable frame 30 has a structure in which the supports 31a and 31b are connected to the ceiling 32 at angles other than right angles. This structure thus causes a difference in height between the connecting position of the support 31a and the ceiling 32 and the connecting position of the support 31b and the ceiling 32 when a force is applied in the X-axis direction. As a result, the ceiling 32 is inclined.

In this way, the variable frame 30 includes the ceiling 32 having an opposed surface 32a facing the light-emitting unit 21, and the pair of supports 31a and 31b that are arranged along the arrangement direction of the pair of light detectors 22b and 22d, and connected to the ceiling 32 at angles other than right angles to support the ceiling 32. The variable frame 30 has a degree of freedom in the arrangement direction of the pair of light detectors 22b and 22d at the connecting portions of the ceiling 32 and the respective supports 31a and 31b.

The variable frame 30 has fixing portions 33 on the negative direction side in the X-axis direction of the support 31a and on the positive direction side in the X-axis direction of the support 31b (refer to FIG. 3A). The fixing portions 33 are used for fixing the variable frame 30 to the base 10.

The mirror 40 is attached to the rear surface (the opposed surface 32a that faces the light-emitting unit 21) of the ceiling 30 of the variable frame 30 (refer to FIG. 3B). The mirror 40 is disposed directly above the light-emitting unit 21 of the displacement sensor 20. The mirror 40 reflects laser light emitted from the light-emitting unit 21 of the displacement sensor 20 such that the reflected light enters the light detectors 22a to 22d.

The ceiling 32 has a width of substantially 6 mm and a length of substantially 18 mm, for example. The height (distance from the fixing portion 33 to the ceiling 32) of the variable frame 30 is 4 mm, for example.

The force sensor 1 according to the first embodiment is structured as described above. The force sensor 1 is built in bedding such as an anti-bedsore mattress or a cushion, for example, and detects shearing force occurring between the bedding and a human body.

Figure 4A:
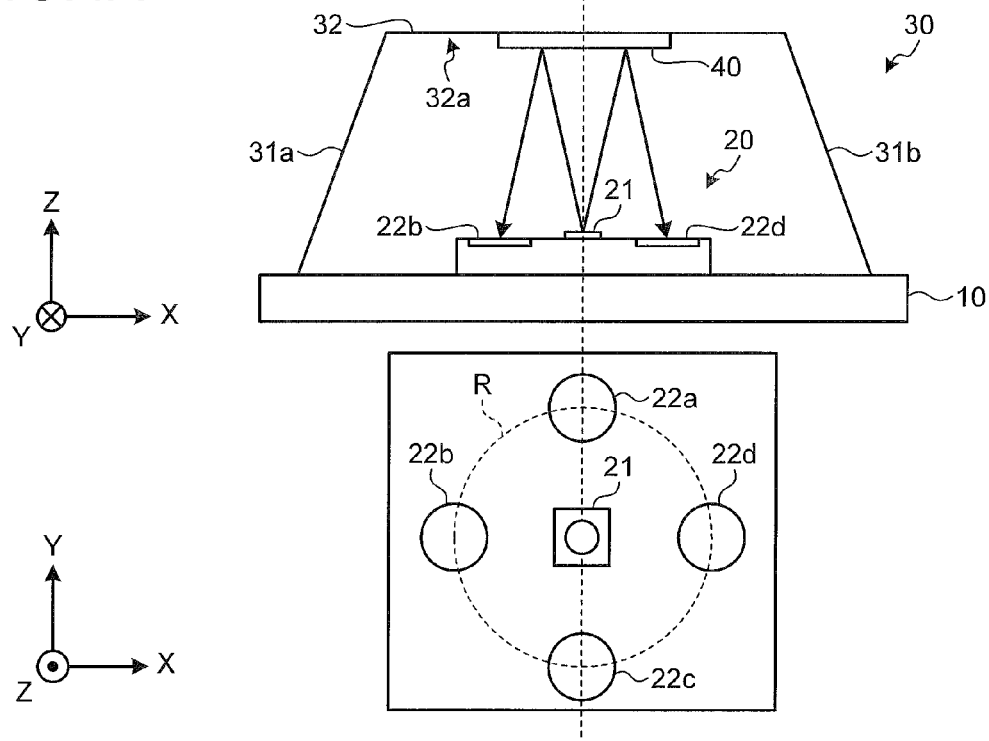
FIG. 4A is an explanatory view of a detection principle of shearing force by the force sensor according to the first embodiment.
Figure 4B:
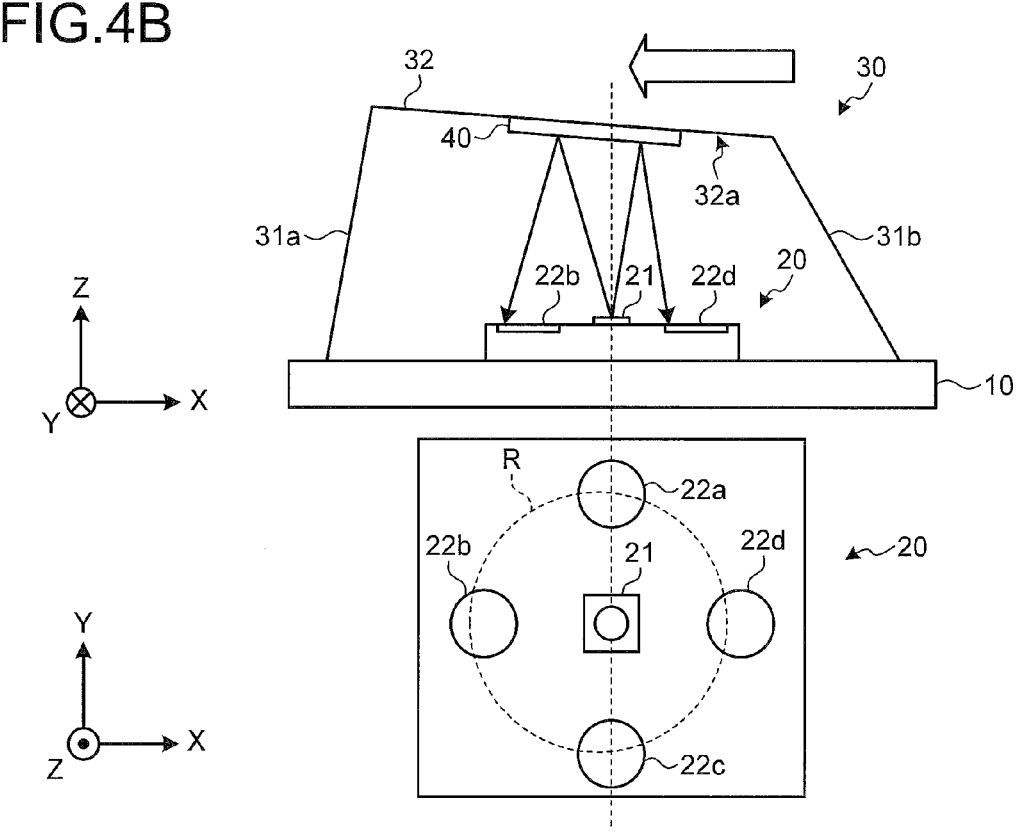
FIG. 4B is another explanatory view of the detection principle of the shearing force by the force sensor according to the first embodiment.

The following describes a detection principle of shearing force by the force sensor 1 with reference to FIGS. 4A and 4B. FIGS. 4A and 4B are explanatory views of the detection principle of shearing force by the force sensor 1 according to the first embodiment. The detection principle is described on the basis of a case where shearing force acting in the X-axis direction is detected using the light detectors 22b and 22d.

As illustrated on the upper side in FIG. 4A, the force sensor 1 according to the first embodiment emits diffuse laser light from the light-emitting unit 21 and reflects the emitted diffuse laser light with the mirror 40. As a result, the displacement sensor 20 is irradiated with the reflected diffuse laser light.

As illustrated on the lower side in FIG. 4A, the light detectors 22a to 22d are arranged such positions that they partially overlap with an irradiation area R of the reflected diffuse laser light, and each detect intensity of received reflected light. As illustrated in FIG. 4A, the center of the irradiation area R coincides with the center of the light-emitting unit 21 in a state where the ceiling 32 of the variable frame 30 is horizontally supported. In the state, the respective light detectors 22a to 22d equally overlap with the irradiation area R to each have the same overlapping area.

As illustrated on the upper side in FIG. 4B, the ceiling 32 is inclined when shearing force in the negative direction of the X axis is applied to the ceiling 32 of the variable frame 30. With the inclination of the ceiling 32, the mirror 40 provided on the ceiling 32 is inclined, thereby displacing the position of the irradiation area R, to which the diffuse laser light is reflected, that is, a destination of reflected diffuse light (refer to the diagram illustrated on the lower side in FIG. 4B).

The displacement of the position of the irradiation area R causes a difference between the area in which the light detector 22b and the irradiation area R overlap with each other and the area in which the light detector 22d and the irradiation area R overlap with each other. As a result, the light detectors 22b and 22d detect reflected light having different intensities.

The force sensor 1 calculates the inclination of the mirror 40 on the basis the difference in intensity of reflected light. Specifically, a value S that indicates the inclination of the mirror 40 is expressed by the following expression: S=(P2−P4)/(P2+P4) where P2 is the output value from the light detector 22b and P4 is the output value from the light detector 22d.

The force sensor 1 includes a conversion processing unit that converts the calculated value S into a shearing force value and outputs the shearing force value. The conversion processing unit converts the value S into a shearing force value using a conversion equation that converts the values S into a shearing force value or a table in which the value S and a shearing force value are associated with each other. The conversion equation and the table values are determined on the basis of actual measurement or structure calculation, for example.

A larger shearing force applied to the variable frame 30 makes the ceiling 32 incline to a greater degree, thereby increasing the inclined angle of the mirror 40. With an increase in the inclined angle of the mirror 40, the difference in output value between the light detectors 22b and 22d is increased, thereby increasing the absolute value of the value S. In this way, the shearing force applied to the variable frame 30 and the value S have a proportional relation with respect to each other. The force sensor 1 can thus detect shearing force applied to the variable frame 30 by detecting the value S.

Figure 5A:
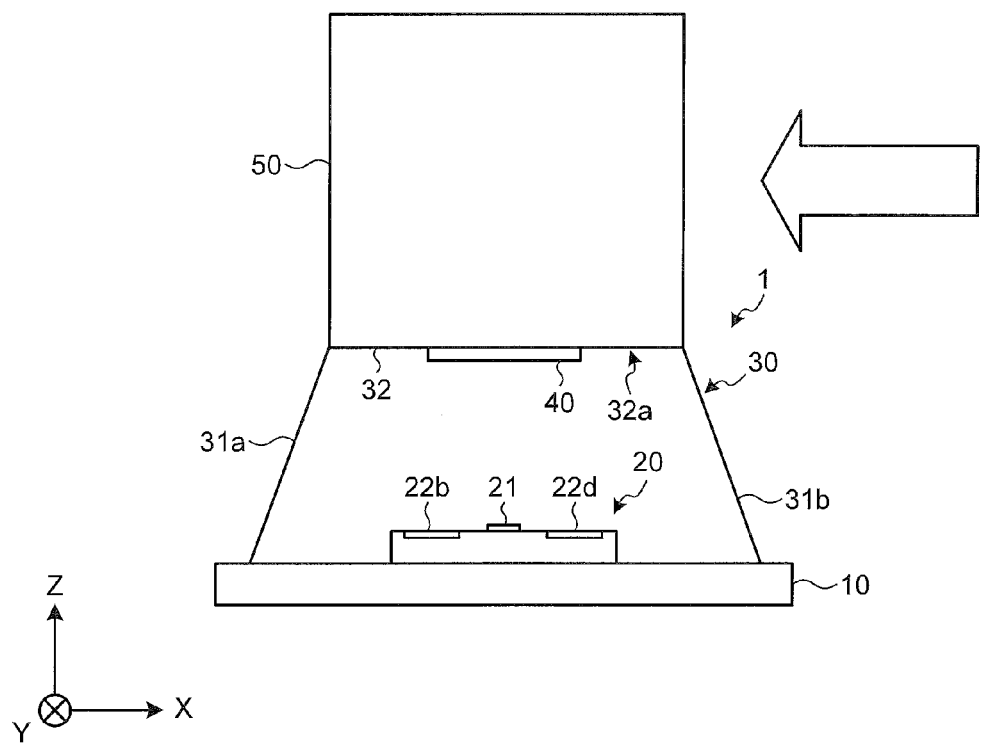
FIG. 5A is a schematic side view of the force sensor to which a force transferring member is attached.
Figure 5B:
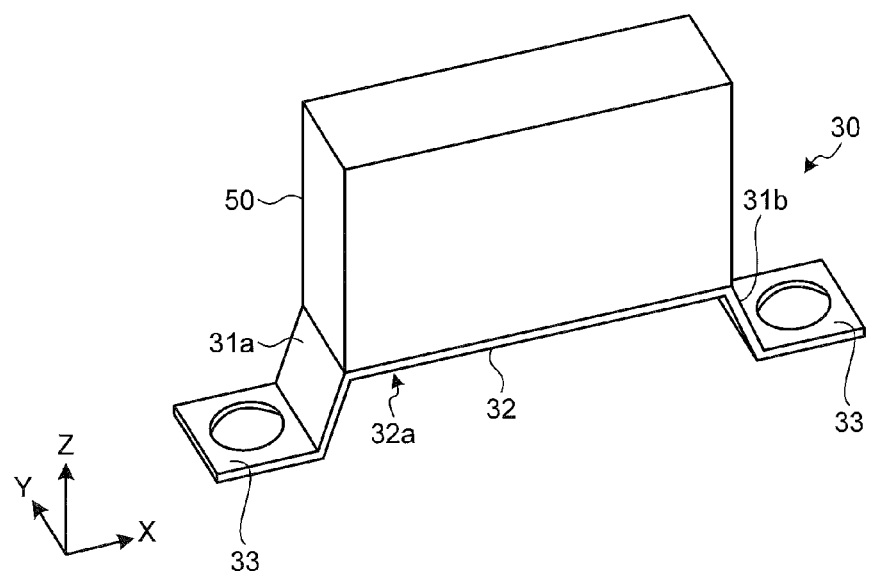
FIG. 5B is a schematic perspective view of the force transferring member and the variable frame.
Figure 6:
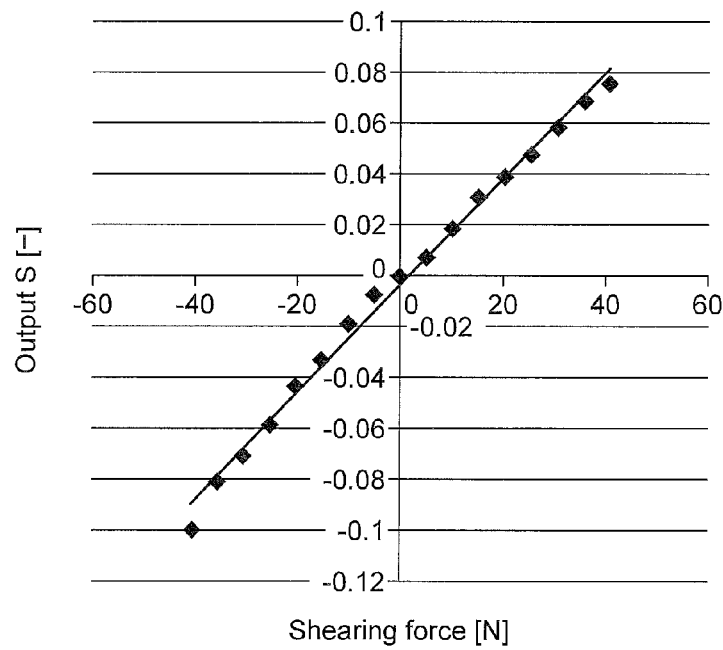
FIG. 6 is a schematic diagram illustrating a change in value S when shearing force is increasingly applied to the force sensor according to the first embodiment in a range from −40N to 40N by 5N.

The following describes the proportional relation in detail with reference to FIGS. 5A, 5B, and 6. FIG. 5A is a schematic side view of the force sensor 1 to which a force transferring member is attached. FIG. 5B is a schematic perspective view of the force transferring member and the variable frame 30. FIG. 6 illustrates a change in value S when shearing force is increasingly applied to the force sensor 1 according to the first embodiment in a range from −40N to 40N by 5N.

As illustrated in FIGS. 5A and 5B, a force transferring member 50 is attached to the top surface of the ceiling 32 so as to accurately apply shearing force to the ceiling 32 of the variable frame 30. The force transferring member 50 has a rectangular parallelepiped shape and transfers externally applied force to the ceiling 32 of the variable frame 30.

Specifically, when the force transferring member 50 is pushed, shearing force is applied to the ceiling 32 of the variable frame 30.

In this case, shearing force acting in the negative direction of the X axis is described as the positive shearing force. For example, a shearing force of 40N applied in the positive direction of the X axis is described as a shearing force of "−40N".

As illustrated in FIG. 6, when the force transferring member 50 is pushed in the negative direction of the X axis, that is, shearing force in the negative direction of the X axis is applied to the ceiling 32 of the variable frame 30, the value S is linearly increased with an increase in shearing force. The reason why the value S is linearly increased is as follows. The force applied to the ceiling 32 in the negative direction of the X axis causes the mirror 40 to be inclined, thereby moving the irradiation area R (refer to FIG. 4A) to the negative direction side in the X-axis direction. As a result, the output value P2 from the light detector 22b becomes larger than the output value P4 from the light detector 22d.

In contrast, when the force transferring member 50 is pushed in the positive direction of the X axis, that is, shearing force in the positive direction of the X axis is applied to the ceiling 32 of the variable frame 30, the value S is linearly decreased with an increase in shearing force. The reason why the value S is linearly decreased is as follows. The force applied to the ceiling 32 in the positive direction of the X axis causes the mirror 40 to be inclined, thereby moving the irradiation area R (see FIG. 4A) to the positive direction side in the X-axis direction. As a result, the output value P2 from the light detector 22b becomes smaller than the output value P4 from the light detector 22d.

As described above, the value S is linearly increased with an increase in shearing force when shearing force is applied to the ceiling 32 of the variable frame 30 in one direction (in this case, in the negative direction of the X axis) while the value S is linearly decreased with an increase in shearing force when shearing force is applied to the ceiling 32 of the variable frame 30 in the other direction (in this case, in the positive direction of the X axis). From the above results, it is understood that the force sensor 1 can detect a direction and a size of shearing force.

As described above, the force sensor 1 according to the first embodiment includes the light-emitting unit 21, the displacement sensor 20, the variable frame 30, and the mirror 40. The light-emitting unit 21 emits diffuse light. The displacement sensor 20 includes the pair of first light detectors 22b and 22d arranged in the first direction with the light-emitting unit 21 interposed therebetween.

The variable frame 30 includes the opposed surface 32a that faces the light-emitting unit 21 on an optical axis of the light-emitting unit 21. The variable frame 30 is fixed to the base 10 that serves as a mounting surface on which the light-emitting unit 21 is mounted. The variable frame 30 has a degree of freedom in the arrangement direction of the pair of first light detectors 22b and 22d. The mirror 40 is provided on the opposed surface 32a facing the light-emitting unit 21 of the variable frame 30 and reflects diffuse light emitted from the light-emitting unit 21 toward the pair of first light detectors 22b and 22d.

In other words, the mirror 40 is arranged to face the light-emitting unit 21 on the optical axis of the light-emitting unit 21, and reflects diffuse light emitted from the light-emitting unit 21 toward the pair of first light detectors 22b and 22d. The variable frame 30 includes the mirror 40 on the opposed surface 32a arranged to face the light-emitting unit 21 on the optical axis of the light-emitting unit 21. The variable frame 30 is fixed to the base 10 that serves as the mounting surface on which the light-emitting unit 21 is mounted. The variable frame 30 is deformed in a manner capable of displacing the destination of diffuse light reflected by the mirror 40 in the first direction. As a result, the force sensor 1 according to the embodiment can detect shearing force occurring between bedding and a human body with a simple stricture.

The force sensor 1 according to the first embodiment uses the displacement sensor 20. The displacement sensor 20 has less variation due to temperature fluctuations and less variation among the displacement sensors 20 than those of a piezoelectric sensor. The force sensor 1 according to the first embodiment can thus accurately detect shearing force regardless of an external environment and a difference among the force sensors 1 compared to a force sensor using the piezoelectric sensor.

Figure 7:
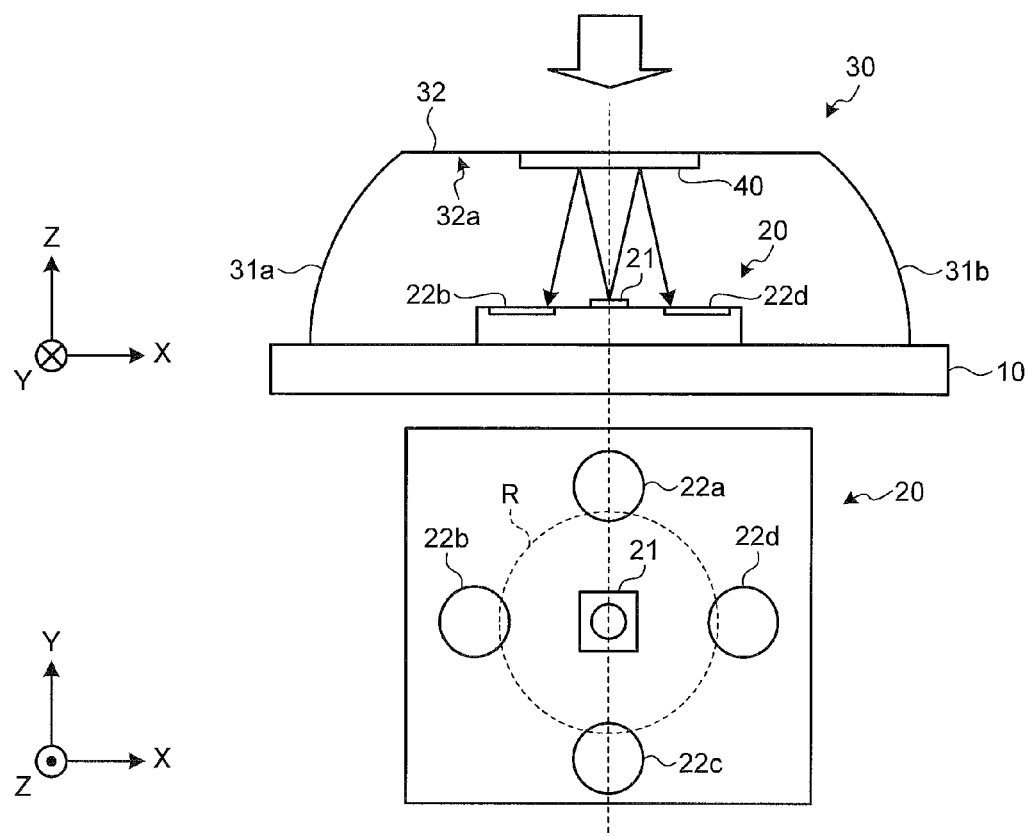
FIG. 7 is an explanatory view of a detection principle of a pressing force by the force sensor according to the first embodiment.

The variable frame 30 has a degree of freedom also in the vertical direction. The force sensor 1 can thus detect a pressing force besides the shearing force. The detection of a pressing force is described below with reference to FIG. 7. FIG. 7 is an explanatory view of a detection principle of a pressing force by the force sensor 1 according to the first embodiment.

As illustrated in FIG. 7, when the variable frame 30 of the force sensor 1 is pressed downward in the vertical direction (the negative direction of the Z axis), the supports 31a and 31b are bent. The ceiling 32 and the mirror 40 thus approach to the displacement sensor 20 while being horizontally supported. As a result, the areas where the respective light detectors 22a to 22d receive reflected diffuse laser light are reduced, thereby uniformly reducing the output values from the respective light detectors 22a to 22d.

An approach of the mirror 40 to the displacement sensor 20, that is, an increase in the pressing force applied to the force sensor 1 in the vertical direction, further uniformly reduces the output values from the respective light detectors 22a to 22d. The force sensor 1 can thus detect a pressing force on the basis of the output values from the respective light detectors 22a to 22d.

The force sensor 1 can also detect torque besides the shearing force and the pressing force. The detection of torque is described with reference to FIGS. 8, 9A, and 9B. The following describes an example where a force is applied to a steering wheel of a vehicle in a direction of rotation of the steering wheel, and torque applied to a steering shaft (hereinafter, described as the "shaft") is detected. The torque detected by the force sensor 1 is not limited to the torque applied to the shaft.

Figure 8:
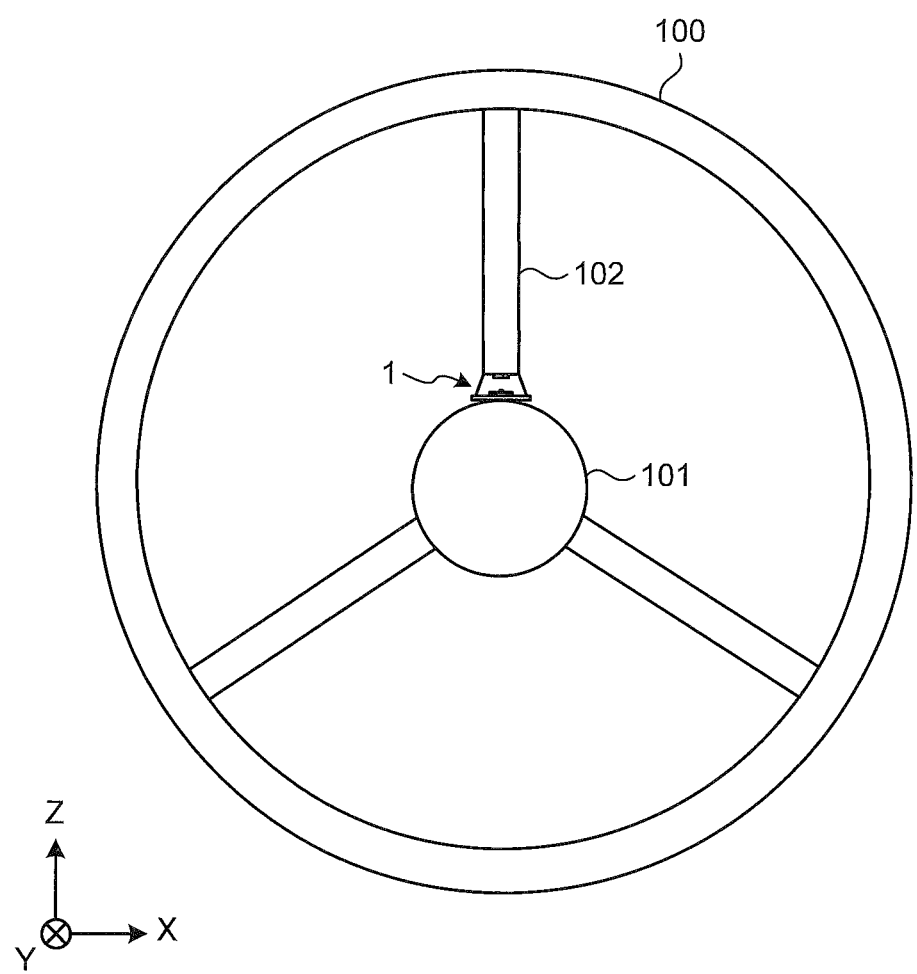
FIG. 8 is an explanatory view illustrating an application example where the force sensor according to the first embodiment is used for detecting torque.

FIG. 8 is an explanatory view illustrating an application example where the force sensor 1 according to the first embodiment is used for detecting torque. FIGS. 9A and 9B are explanatory views of the detection principle of torque by the force sensor 1 according to the first embodiment.

As illustrated in FIG. 8, the force sensor 1 is provided between a shaft 101 and one of steering spokes (hereinafter, described as a "spoke 102") when torque applied to the shat 101 is detected by applying a force in a direction of rotation of a steering wheel 100.

As a result, the force applied in the direction of rotation of the steering wheel 100 is applied to the ceiling 32 (refer to FIG. 1) of the force sensor 1 as torque that causes the shaft 101 to rotate, thereby making it possible for the force sensor 1 to detect the torque applied to the shaft 101.

For example, as illustrated in FIG. 9A, a force F is applied to the edge in the positive direction of the Z axis (hereinafter, described as the "uppermost edge") of the steering wheel 100 in the negative direction of the X axis where the distance from the ceiling 32 of the force sensor 1 to the uppermost edge is r. A force that causes the spoke 102 to rotate counterclockwise is applied to the spoke 102 from the steering wheel 100 while a torque of F×r that causes the ceiling 32 to rotate counterclockwise is applied to the ceiling 32 of the force sensor 1 from the spoke 102.

As a result, the variable frame 30 is deformed in a manner capable of displacing the destination of diffuse light reflected by the mirror 40 in the positive direction of the X axis, as illustrated in FIG. 9B. Specifically, the support 31a is inclined clockwise from the state illustrated in FIG. 9A while the support 31b is inclined counterclockwise from the state illustrated in FIG. 9A. The ceiling 32 is thus displaced from the state illustrated in FIG. 9A, in which the ceiling 32 is horizontally supported, to an inclined state where the ceiling 32 is downwardly inclined toward the negative direction of the X axis.

As a result, the destination of the diffuse light reflected by the mirror 40 is displaced from that illustrated in FIG. 9A to that in the positive direction of the X axis, thereby reducing the intensity of reflected light received by the light detector 22b and increasing the intensity of reflected light received by the light detector 22d. A difference in intensity of received reflected light thus occurs between the light detectors 22b and 22d.

The difference in intensity of received light is increased with an increase in inclination, that is, an inclined angle, of the mirror 40. The inclination of the mirror 40 is increased with an increase in torque applied to the ceiling 32 of the force sensor 1. The force sensor 1 can thus detect the torque applied to the ceiling 32 by calculating the inclination of the mirror 40 on the basis of a difference in intensity of received reflected light between the light detectors 22b and 22d.

As a method for calculating the inclination of the mirror 40, the calculation formula used for calculating the value S, which indicates the inclination of the mirror 40, in detection of shearing force can be used. The calculation formula used for calculating the value S is as follows: $S=(P2-P4)/(P2+P4)$. When the calculated value S is converted into a torque value, the conversion is performed by using a conversion equation that converts the value S into a torque value, or a table in which the value S and a torque value are associated with each other. The conversion equation and the table values are determined on the basis of actual measurement or structure calculation, for example.

As can be understood by the reference to FIG. 9B and FIG. 4B, the direction in which the mirror 40 is inclined is reversed between a case where torque is applied to the force sensor 1 and a case where shearing force is applied to the force sensor 1 when the applying directions of the torque and the shearing force are the same.

As illustrated in FIG. 4B, the mirror 40 is downwardly inclined toward the positive direction of the X axis when shearing force in the negative direction of the X axis is applied to the force sensor 1. As illustrated in FIG. 9B, the mirror 40 is downwardly inclined toward the negative direction of the X axis when torque in the negative direction of the X axis is applied to the force sensor 1.

When torque is detected using the calculation formula used for calculating the value S, torque acting on the force sensor 1 in the positive direction of the axis X, that is, torque causing the steering wheel 100 to rotate clockwise, needs to be defined as the positive torque. In contrast, torque acting on the force sensor 1 in the negative direction of the X axis, that is, torque causing the steering wheel 100 to rotate counterclockwise, is defined as the negative torque.

As described above, the force sensor 1 according to the first embodiment is provided between the shaft 101 and the spoke 102 to which a force causing the shaft 101 to rotate is applied, thereby making it possible to detect the torque applied to the shaft 101. The force sensor 1 is provided between any rotating body and a member that applies torque causing the rotating body to rotate, thereby making it possible to detect the torque applied to the rotating body.

For the force sensor 1, sensitivity in detecting torque and a measurement range of torque can be changed by changing the material of the variable frame 30 and inner angles made by the ceiling 32 of the variable frame 30 and the respective supports 31a and 31b.

The following describes how the torque detection sensitivity and the measurement range are changed with reference to FIGS. 10, 11A, 11B, 12A, and 12B. The following description is made with reference to the results of an experiment in which the variable frames 30 having different materials and different inner angles made by the ceiling 32 and the respective supports 31a and 31b are used, and torque is detected by the force sensor 1 using each of the variable frames 30.

FIG. 10 is an explanatory view illustrating an example of experiment conditions on torque detection by the force sensor 1 according to the first embodiment. FIGS. 11A to 12B are explanatory views illustrating exemplary experiment results on torque detection by the force sensor 1 according to the first embodiment.

In the torque detection experiment, torque was detected by the force sensor 1 under four experiment conditions (a) to (d) as illustrated in FIG. 10. Specifically, in the experiment conditions (a) and (b), the variable frames 30 made of stainless steel were used, while, in the experiment conditions (c) and (d), the variable frames 30 made of copper were used. As can be understood from the Young's modulus illustrated in FIG. 10, the variable frame made of copper has a higher elasticity than that of the variable frame made of stainless steel.

In the experiment condition (a), an inner angle made by the ceiling 32 of the variable frame 30 and the support 31a was 105 degrees while an inner angle made by the ceiling 32 of the variable frame 30 and the support 31b was 110 degrees. In the experiment condition (b), an inner angle made by the ceiling 32 of the variable frame 30 and the support 31a was 115 degrees while an inner angle made by the ceiling 32 of the variable frame 30 and the support 31b was 120 degrees.

In the experiment condition (c), an inner angle made by the ceiling 32 of the variable frame 30 and the support 31a was 111 degrees while an inner angle made by the ceiling 32 of the variable frame 30 and the support 31b was 112 degrees. In the experiment condition (d), an inner angle made by the ceiling 32 of the variable frame 30 and the support 31a was 118 degrees while an inner angle made by the ceiling 32 of the variable frame 30 and the support 31b was 122 degrees. As described above, the inner angles made by the ceiling 32 of the variable frame 30 and the respective supports 31a and 31b are larger than 90 degrees in the experiment conditions (a) to (d).

In the experiment conditions (a) and (b), torque was applied to the force sensor 1 in a range from −0.3 Nm to 0.3 Nm and the force sensor 1 detected the torque. In the experiment conditions (c) and (d), torque was applied to the force sensor 1 in a range from −0.2 Nm to 0.2 Nm and the force sensor 1 detected the torque.

When a force causing the steering wheel 100 to rotate clockwise is applied, the force sensor 1 detects torque as the positive torque while when a force causing the steering wheel 100 to rotate counterclockwise is applied, the force sensor 1 detects torque as the negative torque.

Figure 11A:
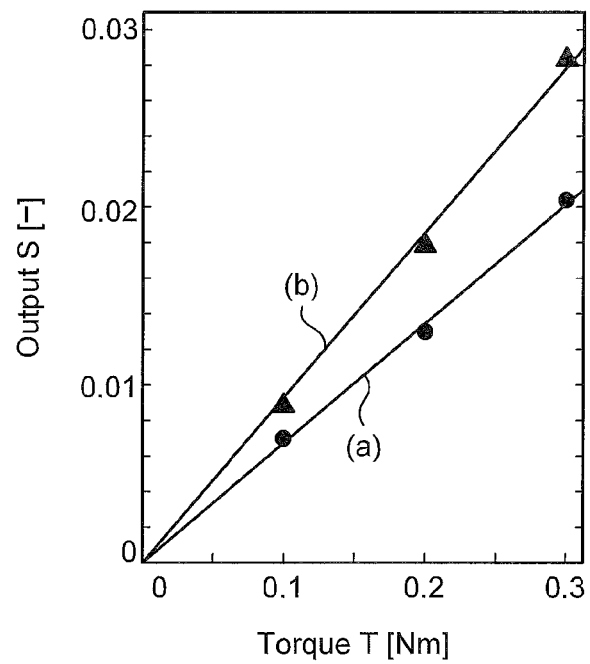
FIG. 11A is an explanatory view illustrating an example of experiment results on torque detection by the force sensor according to the first embodiment.
Figure 11B:
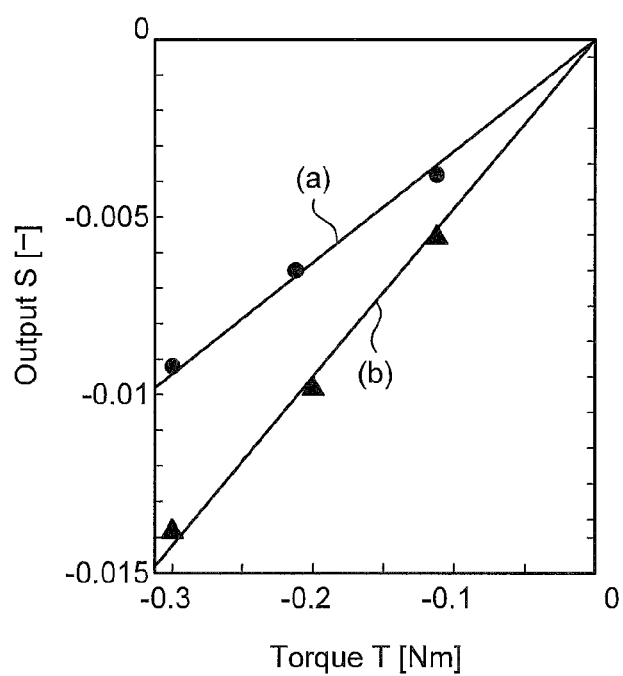
FIG. 11B is another explanatory view illustrating the example of the experiment results on torque detection by the force sensor according to the first embodiment.
Figure 12A:
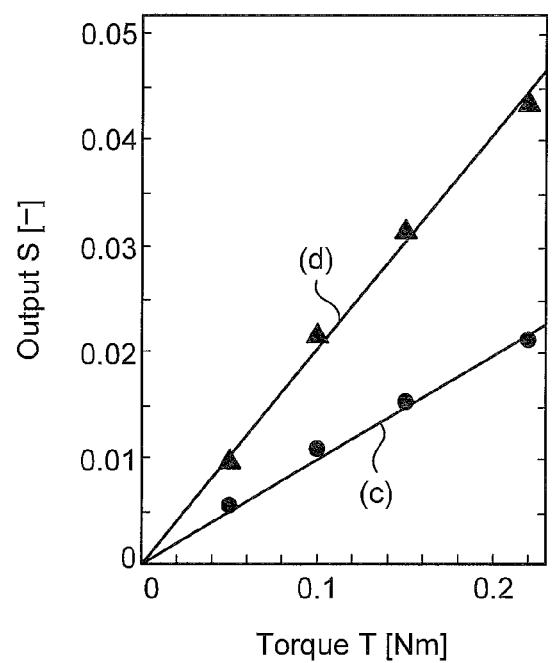
FIG. 12A is another explanatory view illustrating the example of the experiment results on torque detection by the force sensor according to the first embodiment.
Figure 12B:
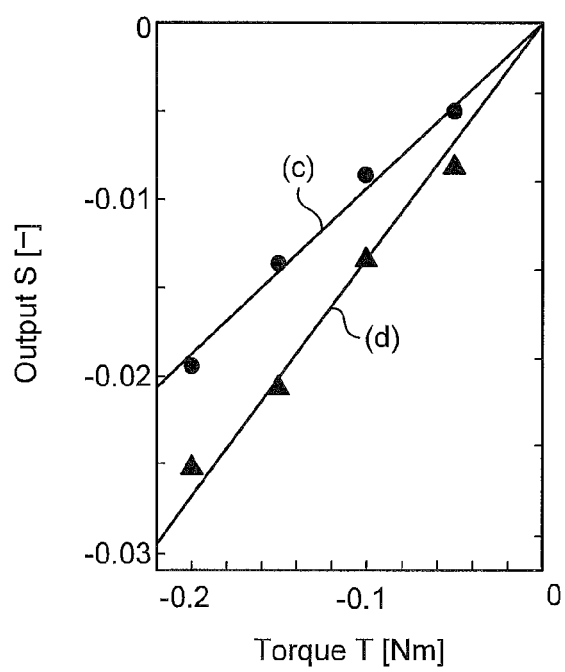
FIG. 12B is another explanatory view illustrating the example of the experiment results on torque detection by the force sensor according to the first embodiment.

The circular dots plotted in FIGS. 11A and 11B illustrate the experiment result under the experiment condition (a) while the triangles plotted in FIGS. 11A and 11B illustrate the experiment result under the experiment condition (b). In FIGS. 12A and 12B, the plotted circular dots illustrate the experiment result under the experiment condition (c) while the plotted triangles illustrate the experiment result under the experiment condition (d). The abscissa axis in the graph illustrated in each of FIGS. 11A to 12B represents the torque applied to the force sensor 1 while the vertical axis in the graph illustrated in each of FIGS. 11A to 12B represents the value S that indicates the inclination of the mirror 40.

As illustrated in FIGS. 11A to 12B, larger inner angles made by the ceiling 32 of the variable frame 30 and the respective supports 31a and 31b increase the amount of change in inclination angle of the ceiling 32 with respect to the amount of change in applied torque when the variable frames 30 are made of the same material. Larger inner angles made by the ceiling 32 and the respective supports 31a and 31b increase the torque detection sensitivity of the force sensor 1 when the variable frames 30 used for the force sensor 1 are made of the same material.

Smaller inner angles made by the ceiling 32 and the respective supports 31a and 31b increase the range of the inclination angle of the ceiling 32 when the variable frames 30 are made of the same material. Smaller inner angles made by the ceiling 32 and the respective supports 31a and 31b increase the torque measurement range of the force sensor 1 when the variable frames 30 used for the force sensor 1 are made of the same material.

When the variable frames 30 are made of different materials, higher elasticity of the ceiling 32 of the variable frame 30 increases the inclination of the ceiling 32 with respect to the same applied torque. Higher elasticity of the material increases the torque detection sensitivity of the force sensor 1 when the variable frames 30 used for the force sensor 1 are made of different materials.

As described above, the torque detection sensitivity and the torque measurement range of the force sensor 1 according to the first embodiment can be changed by changing the material of the variable frame 30 or the inner angles made by the ceiling 32 of the variable frame 30 and the respective supports 31a and 31b.

Figure 13:
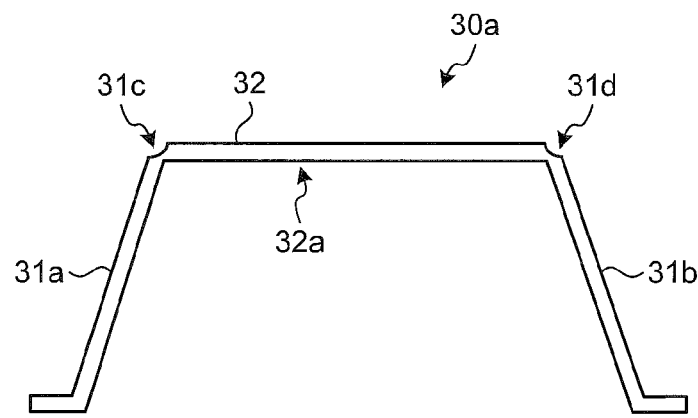
FIG. 13 is a schematic side view of a variable frame that increases sensitivity of the force sensor according to the first embodiment.

The method for changing the sensitivity of the force sensor 1 is not limited to the manner described above. FIG. 13 is a schematic side view of a variable frame 30a that increases the sensitivity of the force sensor 1 according to the first embodiment. As illustrated in FIG. 13, the variable frame 30a has a thin portion 31c at the connecting portion of the support 31a and the ceiling 32 and a thin portion 31d at the connecting portion of the support 31b and the ceiling 32, the thin portions being thinner than other portions.

In the variable frame 30a, smaller thicknesses of the thin portions 31c and 31d reduce the torque that causes the ceiling 32 to be inclined. The sensitivity of the force sensor 1 including the variable frame 30a is changed with a change in the thicknesses of the thin portions 31c and 31d. Smaller thicknesses of thin portions 31c and 31d increase the torque detection sensitivity of the force sensor 1.

As described above, the torque detection sensitivity and the torque measurement range of the force sensor 1 can be changed by changing the material and shape of the variable frame 30. In addition, for the force sensor 1, the sensitivity in detecting shearing force and the measurement range of shearing force can be changed by changing the material and shape of the variable frame 30.

For example, when detecting shearing force, smaller inner angles made by the ceiling 32 and the respective supports 31a and 31b increase the shearing force detection sensitivity of the force sensor 1, which is reversed from the way for detecting torque. Higher elasticity of the material used for the variable frame 30 increases the shearing force detection sensitivity of the force sensor 1.

In the force sensor 1 including the variable frame 31a, smaller thicknesses of the thin portions 31c and 31d increase the shearing force detection sensitivity in the same manner as the case where the torque is detected.

When detecting shearing force, smaller inner angles made by the ceiling 32 and the respective supports 31a and 31b increase the torque measurement range of the force sensor 1 in the same manner as the case where the torque is detected.

Second Embodiment

Figure 14:
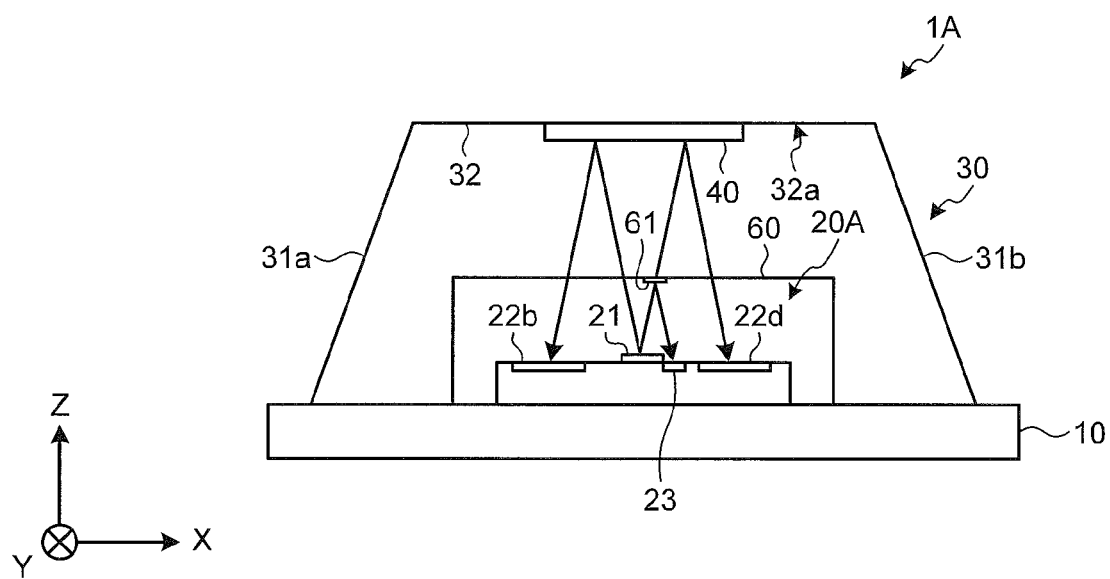
FIG. 14 is a schematic side view of a force sensor according to a second embodiment.

The displacement sensor 20 may further include a light detector for monitoring to feedback an output of diffuse laser light emitted from the light-emitting unit 21. The following describes an example where the displacement sensor 20 includes a light detector for monitoring with reference to FIG. 14. FIG. 14 is a schematic side view of a force sensor according to a second embodiment. In the following description, the same components described in the first embodiment are labeled with the same reference numerals and duplicated descriptions thereof are omitted.

As illustrated in FIG. 14, a force sensor 1A according to the second embodiment includes a displacement sensor 20A instead of the displacement sensor 20 according to the first embodiment. The force sensor 1A according to the second embodiment further includes a cover 60.

The cover 60 is a transparent member that has a box shape and seals the displacement sensor 20A. The cover 60, which seals the displacement sensor 20A, allows diffuse laser light emitted from the light-emitting unit 21 to be transmitted, protects the displacement sensor 20A from humidity, and hermetically seals the displacement sensor 20A. On the ceiling of the cover 60, a reflecting member 61 such as gold foil is provided.

The displacement sensor 20A further includes a light detector 23 for monitoring besides the structure of the displacement sensor 20. As the light detecting unit 23 for monitoring, a photo diode can be used, for example. The light detector 23 for monitoring is disposed near the light-emitting unit 21 and detects the intensity of diffuse laser light reflected by the reflecting member 61 of the cover 60.

The force sensor 1A according to the second embodiment can feedback the output of diffuse laser light by detecting diffuse laser light that is emitted from the light-emitting unit 21 and reflected by the reflecting member 61 using the light detector 23 for monitoring. As a result, the temperature of diffuse laser light and a change in output of diffuse laser light due to the operating time can be monitored, for example.

Third Embodiment

In the embodiments described above, shearing force acting along the X-axis direction is detected by the first light detectors 22b and 22d arranged along the X-axis direction. The force sensor according to the embodiments can detect not only shearing force acting in the X-axis direction but also shearing force acting in the Y-axis direction further using the second light detectors 22a and 22c on the basis of the detection principle described above.

Figure 15:
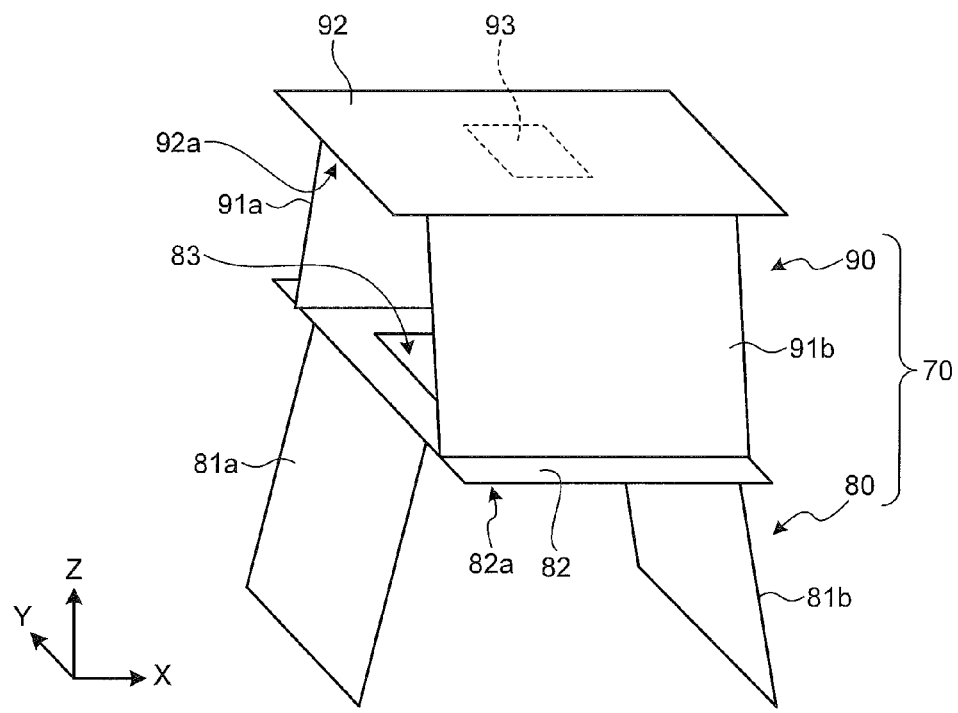
FIG. 15 is a schematic perspective view of a variable frame according to a third embodiment.

In such a case, a variable frame that is deformable in both of the X-axis and the Y-axis directions is used instead of the variable frame 30. The following describes an exemplary structure of the variable frame that is deformable in both of the X-axis and the Y-axis directions with reference to FIG. 15. FIG. 15 is a schematic perspective view of a variable frame according to a third embodiment.

As illustrated in FIG. 15, a variable frame 70 according to the third embodiment has a structure in which a second frame 90 having a degree of freedom in the Y-axis direction is layered on a first frame 80 having a degree of freedom in the X-axis direction.

The first frame 80 and the second frame 90 each have the same basic structure as that of the variable frame 30 according to the first and the second embodiments. Specifically, the first frame 80 includes first legs (hereinafter, described as "supports 81a and 81b") and a ceiling 82. The supports 81a and 81b are inclined with respect to the vertical direction (Z-axis direction). The ceiling 82 is horizontally supported by the supports 81a and 81b. The ceiling 82 includes a first opposed surface 82a that is supported by the supports 81a and 81b such that the first opposed surface 82a faces the light-emitting unit 21 on the optical axis of the light-emitting unit 21.

The second frame 90 includes second legs (hereinafter, described as "supports 91a and 91b") and a ceiling 92. The supports 91a and 91b are inclined with respect to the vertical direction (Z-axis direction). The ceiling 92 is horizontally supported by the supports 91a and 91b. The ceiling 92 includes a second opposed surface 92a that is supported by the supports 91a and 91b such that the second opposed surface 92a faces the light-emitting unit 21 on the optical axis of the light-emitting unit 21.

The supports 81a and 81b of the first frame 80 are arranged along the X-axis direction. The first frame 80 is thus deformed along the X-axis direction when a force is applied in the X-axis direction. The supports 91a and 91b of the second frame 90 are arranged along the Y-axis direction. The second frame 90 is thus deformed along the Y-axis direction when a force is applied in the Y-axis direction.

The first frame 80 has an opening 83 formed on the ceiling 82. The second frame 90 has a mirror 93 provided on the ceiling 92. The variable frame 70 thus allows diffuse laser light emitted from the light-emitting unit 21, which is included in the displacement sensors 20 and 20A, to pass through the opening 83 and enter the mirror 93, and light reflected by the mirror 93 to travel toward the displacement sensor 20 or 20A.

In the variable frame 70, the mirror 93 is supported by the first frame 80 and the second frame 90 and is arranged to face the light-emitting unit 21 on the optical axis of the light-emitting unit 21, and reflects diffuse light.

The first frame 80 is deformed in a manner capable of displacing the destination of diffuse light reflected by the mirror 93 in the X-axis direction. The second frame 90 is deformed in a manner capable of displacing the destination of diffuse light reflected by the mirror 93 in the Y-axis direction.

The force sensor including the variable frame 70 can thus detect shearing forces in both of X-axis and the Y-axis directions. Specifically, when a force is applied in the X-axis direction, the first frame 80 of the variable frame 70 is deformed in a manner capable of displacing the destination of diffuse light reflected by the mirror 93 in the Y-axis direction, thereby making it possible to detect shearing force acting in the X-axis direction by the light detectors 22b and 22d (refer to FIG. 2).

When a force is applied in the Y-axis direction, the second frame 90 of the variable frame 70 is deformed in a manner capable of displacing the destination of diffuse light reflected by the mirror 93 in the Y-axis direction, thereby making it possible to detect shearing force acting in the Y-axis direction by the light detectors 22a and 22c (refer to FIG. 2).

In the third embodiment, the variable frame 70, in which the ceiling 82 of the first frame 80 supports the second frame 90, makes it possible to detect shearing forces in two directions perpendicular to each other. The variable frame that can detect shearing forces in two directions perpendicular to each other is not limited to this example. Another example is described in a fourth embodiment.

Fourth Embodiment

Figure 16:
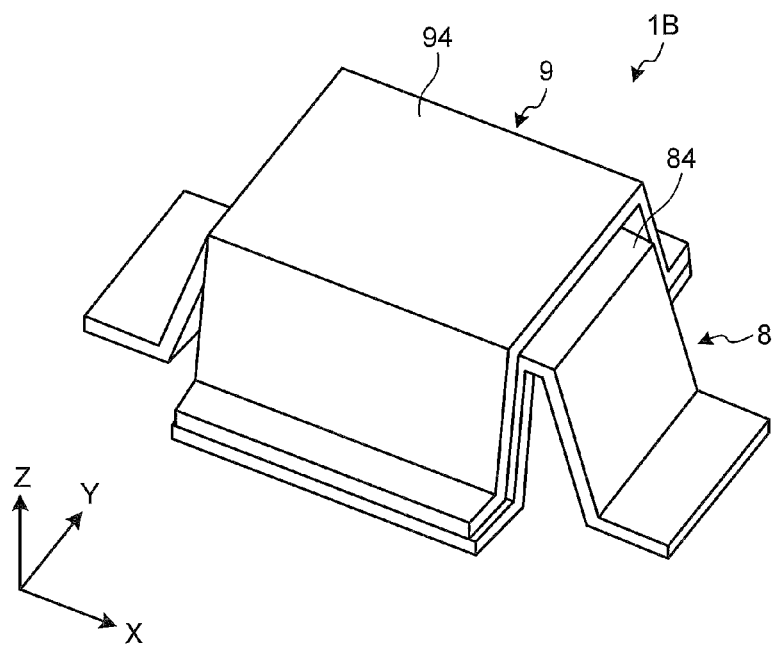
FIG. 16 is a schematic perspective view of a force sensor according to a fourth embodiment.
Figure 17:
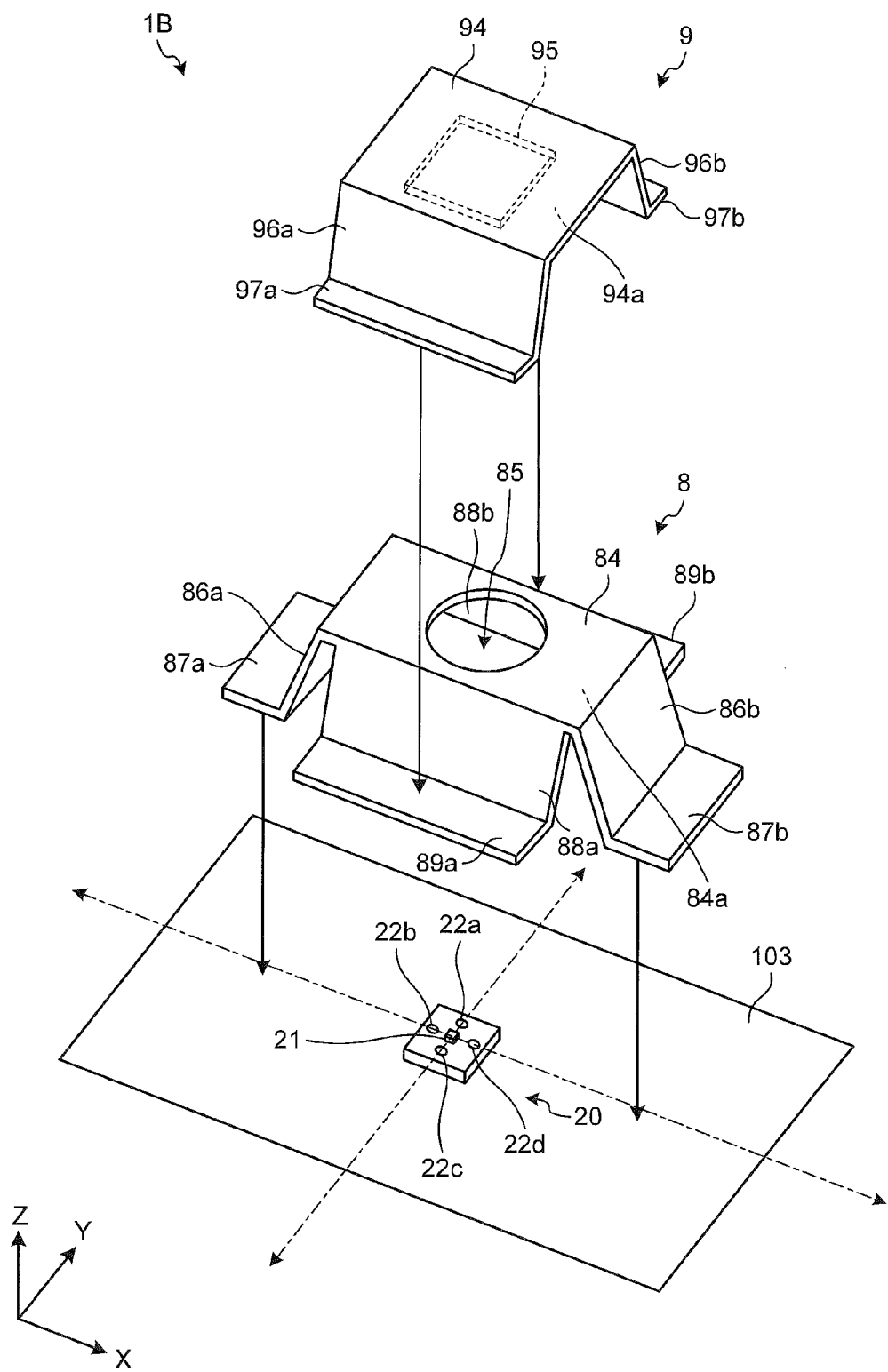
FIG. 17 is a schematic exploded perspective view of the force sensor according to the fourth embodiment.

FIG. 16 is a schematic perspective view of a force sensor 1B according to the fourth embodiment. FIG. 17 is a schematic exploded perspective view of the force sensor 1B according to the fourth embodiment. As illustrated in FIG. 16, the force sensor 1B includes a first frame 8 and a second frame 9 that have different shapes from those of the frames included in the variable frame 70 according to the third embodiment.

In the force sensor 1B, the second frame 9 is also layered on the first frame 8. In the third embodiment, the second frame 90 is supported by the ceiling 82 of the first frame 80, whereas, in the fourth embodiment, the second frame 9 is supported by the first frame 8 on a side closer to a mounting surface on which the force sensor 1B is mounted than to the ceiling 84 of the first frame 8. As a result, the thickness of the force sensor 1B in the Z-axis direction can be further reduced.

Specifically, as illustrated in FIG. 17, the force sensor 1B includes the displacement sensor 20, the first frame 8, and the second frame 9. The displacement sensor 20 is placed on a mounting surface 103 on which the force sensor 1B is mounted. The displacement sensor 20 has the same structure as that described in the first embodiment. The same numerals as those of the first embodiment are thus labeled and the descriptions thereof are omitted.

The first frame 8 includes a pair of first legs 86a and 86b and the ceiling 84 having a first opposed surface 84a. The pair of first legs 86a and 86b is fixed to the mounting surface 103 on which the light-emitting unit 21 is mounted. The first opposed surface 84a is supported by the first legs 86a and 86b such that the first opposed surface 84a faces the light-emitting unit 21 on the optical axis of the light-emitting unit 21.

The first legs 86a and 86b are provided on both sides of the first opposed surface 84a in the first direction (in this case, in the X-axis direction). On the first opposed surface 84a, an opening 85 is provided in an area including a position intersecting with the optical axis of the light-emitting unit 21.

The first frame 8 further includes a pair of connecting arms 88a and 88b that are provided on both sides of the first opposed surface 84a in the second direction (in this case, in the Y-axis direction). The connecting arms 88a and 88b are provided such that they are downwardly inclined from the first opposed surface 84a toward the mounting surface 103.

The first frame 8 is fixed to the mounting surface 103 with a lower end portion 87a of the first leg 86a and a lower end portion 87b of the first leg 86b. When the first frame 8 is fixed to the mounting surface 103, the lower end portions 89a and 89b of the connecting arms 88a and 88b are positioned above the mounting surface 103.

The second frame 9 includes a pair of second legs 96a and 96b that are connected to the first frame 8, and a second opposed surface 94a. The second opposed surface 94a is supported by the second legs 96a and 96b such that the second opposed surface 94a faces the light-emitting unit 21 on the optical axis of the light-emitting unit 21 through the opening 85 of the first opposed surface 84a.

The second legs 96a and 96b are provided on both sides of the second opposed surface 94a in the second direction. A lower end portion 97a of the second leg 96a is connected to a lower end portion 89a of the connecting arm 88a of the first arm 8, and a lower end portion 97b of the second leg 96b is connected to a lower end portion 89b of the connecting arm 88b of the first frame 8 on a side closer to the mounting surface 103 on which the light-emitting unit 21 is placed than to the first opposed surface 84a. A mirror 95 serving as a reflector of the force sensor 1B is provided, on the second opposed surface 94a, in an area including a position intersecting with the optical axis of the light-emitting unit 21.

The first frame of the force sensor 1B is deformed in a manner capable of displacing the destination of diffuse light reflected by the mirror 95 in the first direction when shearing force in the first direction is applied to the ceiling 94 of the second frame 9. In contrast, the second frame 9 of the force sensor 1B is deformed in a manner capable of displacing the destination of diffuse light reflected by the mirror 95 in the second direction when shearing force in the second direction is applied to the ceiling 94 of the second frame 9. The following describes the operation of the force sensor 1B with reference to FIGS. 18A to 19B.

Figure 18A:
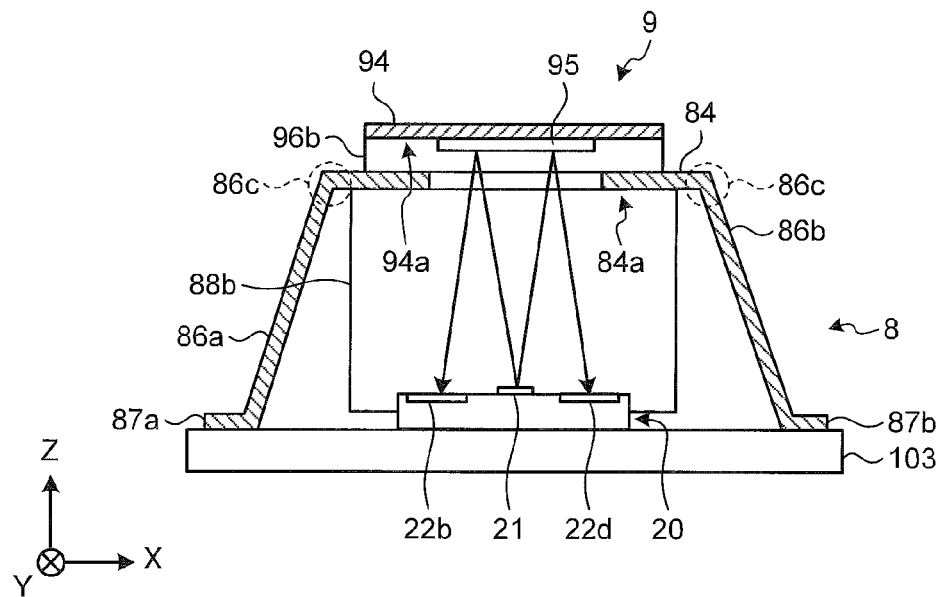
FIG. 18A is a schematic side view illustrating operation of the force sensor according to the fourth embodiment.

FIGS. 18A, 18B, 19A, and 19B are schematic side views illustrating the operation of the force sensor 1B according to the fourth embodiment. As illustrated in FIG. 18A, when no shearing force in the X-axis direction is applied, the ceiling 84 of the first frame 8 and the ceiling 94 of the second frame 9 are kept in parallel with the mounting surface 103. As a result, the mirror 95 reflects diffuse light such that reflected diffuse light partially overlaps with the respective light receiving areas of the first light detectors 22b and 22d to each have the same overlapping area.

Figure 18B:
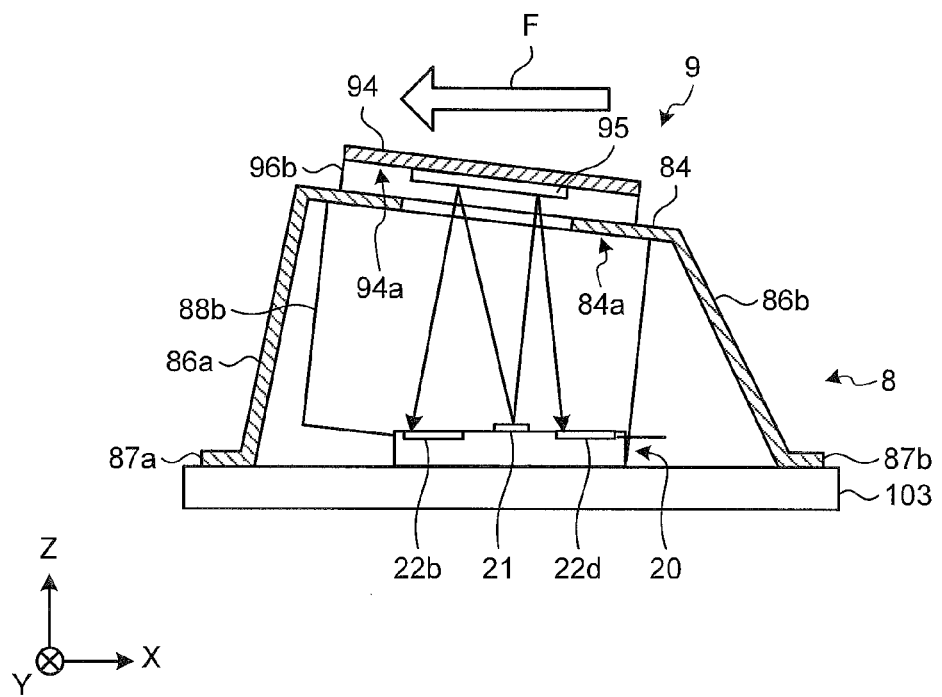
FIG. 18B is another schematic side view illustrating the operation of the force sensor according to the fourth embodiment.

As illustrated in FIG. 18B, when a shearing force F in the negative direction of the X axis is applied to the ceiling 94 of the second frame 9, for example, the first frame 8 is deformed in a manner capable of displacing the destination of diffuse light reflected by the mirror 95 in the negative direction of the X axis.

Specifically, when the shearing force F in the negative direction of the X axis is applied to the ceiling 94 of the second frame 9, the ceiling 94 of the second frame 9 is moved in the negative direction of the X axis. The second frame 9 is fixed to the first frame 8 with the lower end portions 97a and 97b of the second legs 96a and 96b by being connected to the connecting arms 88a and 88b of the first frame 8. In this state, the connecting arms 88a and 88b are positioned above the mounting surface 103.

As a result, the ceiling 84 of the first frame 8 is moved in the negative direction of the X axis together with the ceiling 94 of the second frame 9. The first frame 8 is fixed to the mounting surface 103 with the lower end portion 87a of the first leg 86a and the lower end portion 87b of the first leg 86b. Consequently, with the movement of the ceiling 84 of the first frame 8 in the negative direction of the X axis, the first legs 86a and 86b of the first frame 8 are inclined counterclockwise while maintaining their lengths.

With this inclination, the first opposed surface 84a and the second opposed surface 94a are downwardly inclined toward the positive direction of the X axis, thereby displacing the destination of diffuse light reflected by the mirror 95 in the negative direction of the X axis. In the first frame 8, connecting portions 86c of the first opposed surface 84a and the respective first legs 86a and 86b are deformed, the connecting portions 86c having connecting angles other than right angles, by the shearing force in the negative direction of the X axis, such that the destination of diffuse light reflected by the mirror 95 is displaced in the negative direction of the X axis.

This displacement results in a difference in intensity of diffuse light received by the first light detectors 22b and 22d. The force sensor 1B can thus detect the shearing force acting in the X-axis direction on the basis of the difference in intensity of received light and the same principle used in the first embodiment.

Figure 19A:
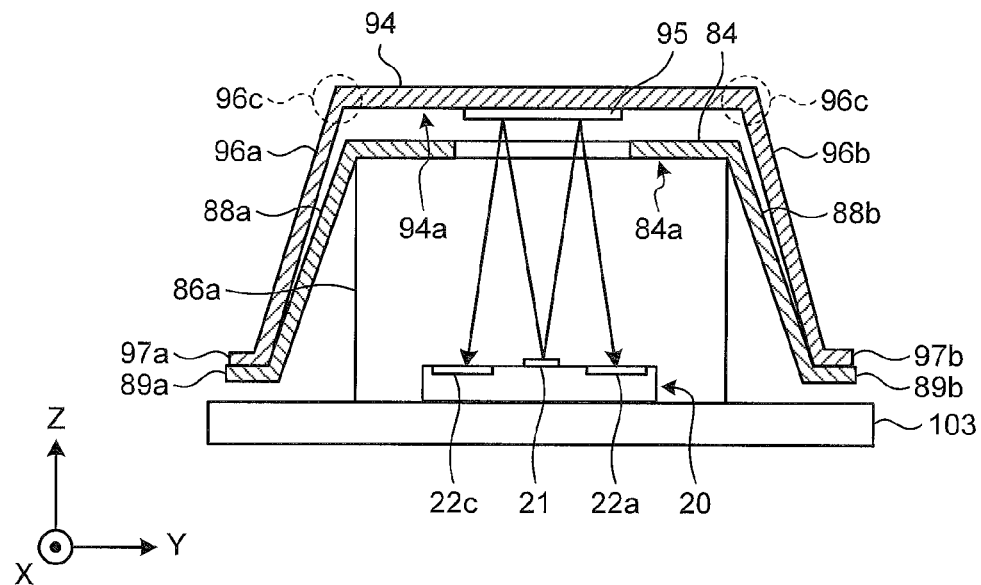
FIG. 19A is another schematic side view illustrating the operation of the force sensor according to the fourth embodiment.

As illustrated in FIG. 19A, when no shearing force in the Y-axis direction is applied, the ceiling 84 of the first frame 8 and the ceiling 94 of the second frame 9 are kept in parallel with the mounting surface 103. As a result, the mirror 95 reflects diffuse light such that reflected diffuse light partially overlaps with the respective light receiving areas of the second light detectors 22c and 22a to each have the same overlapping area.

Figure 19B:
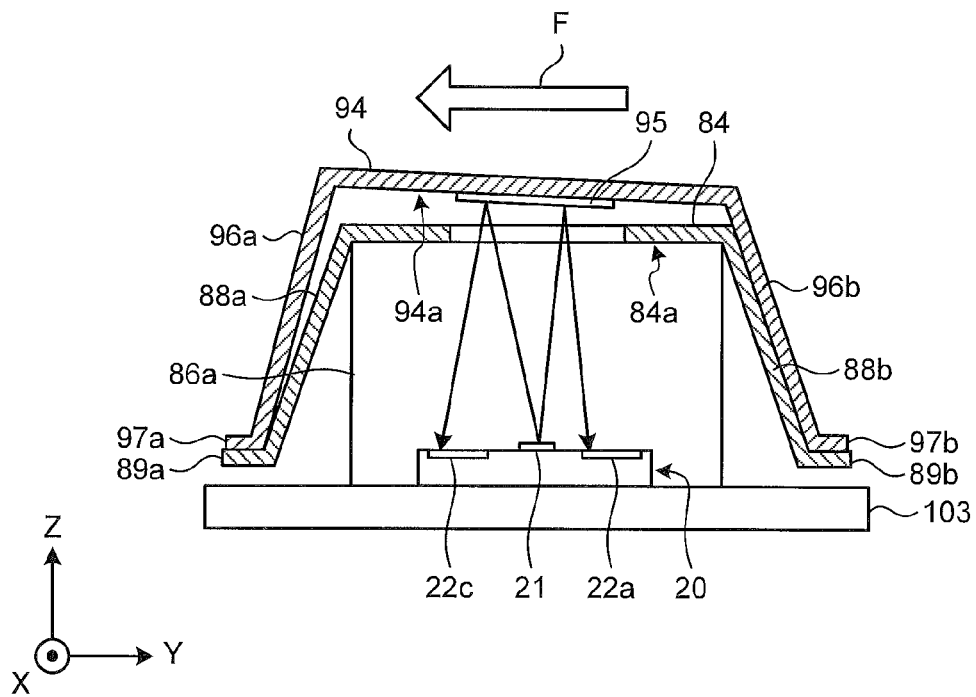
FIG. 19B is another schematic side view illustrating the operation of the force sensor according to the fourth embodiment.

As illustrated in FIG. 19B, when a shearing force F in the negative direction of the Y axis is applied to the ceiling 94 of the second frame 9, for example, the second frame 9 is deformed in a manner capable of displacing the destination of diffuse light reflected by the mirror 95 in the negative direction of the Y axis.

Specifically, when the shearing force F in the negative direction of the Y axis is applied to the ceiling 94 of the second frame 9, the ceiling 94 of the second frame 9 is moved in the negative direction of the Y axis. The second frame 9 is fixed to the first frame 8 with the lower end portions 97a and 97b of the second legs 96a and 96b by being connected to the connecting arms 88a and 88b of the first frame 8. The first frame 8 is fixed to the mounting surface 103 with the lower end portion 87a of the first leg 86a and the lower end portion 87b of the first leg 86b.

With this structure, the ceiling 94 of the second frame 9 is moved in the negative direction of the Y axis whereas the ceiling 84 of the first frame 8 is not moved. Consequently, with the movement of the ceiling 94 of the second frame 9 in the negative direction of the Y axis, the second legs 96a and 96b of the second frame 9 are inclined counterclockwise while maintaining their lengths.

With this inclination, the second opposed surface 94a is downwardly inclined toward the positive direction of the Y axis, thereby displacing the destination of diffuse light reflected by the mirror 95 in the negative direction of the Y axis. In the second frame 9, connecting portions 96c of the second opposed surface 94a and the respective second legs 96a and 96b are deformed, the connecting portions 96c having connecting angles other than right angles, by the shearing force in the negative direction of the Y axis, such that the destination of diffuse light reflected by the mirror 95 is displaced in the negative direction of the Y axis.

This results in a difference in intensity of diffuse light received by the second light detectors 22c and 22a. The force sensor 1B can thus detect the shearing force F acting in the Y-axis direction on the basis of the difference in intensity of received light and the same principle used in the first embodiment. In this way, the force sensor 1B according to the fourth embodiment can also detect shearing forces acting in two directions perpendicular to each other.

In the force sensor 1B, the second frame 9 is supported by the first frame 8 on a side closer to the mounting surface 103 on which the force sensor 1B is placed than to the ceiling 84 of the first frame 8. As a result, the thickness of the force sensor 1B in the Z-axis direction can be further reduced.

The further reduction of the thickness in the Z-axis direction makes it possible to lower the center of gravity of the force sensor 1B. For example, when the force sensor 1B is provided on an inclined mounting surface, the force sensor 1B can detect shearing force with high accuracy by suppressing the deformations of the first frame 8 and the second frame 9 as much as possible.

Fifth Embodiment

Figure 20:
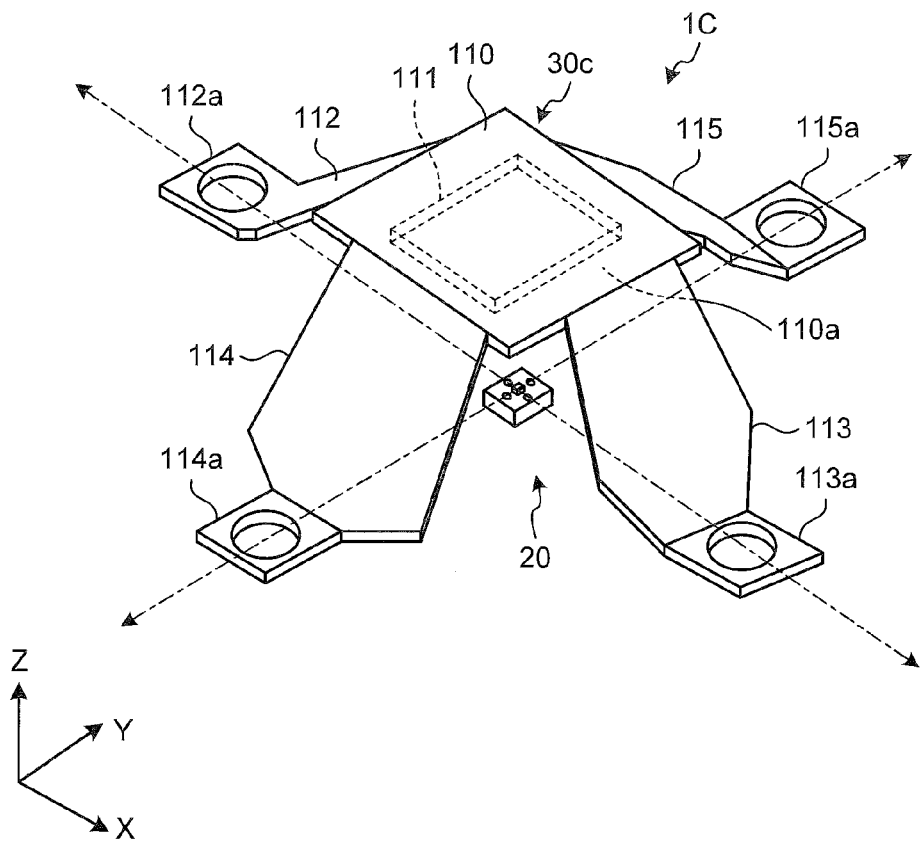
FIG. 20 is a schematic perspective view of a force sensor according to a fifth embodiment.

The following describes a force sensor 1C according to a fifth embodiment with reference to FIG. 20. FIG. 20 is a schematic perspective view of the force sensor 1C according to the fifth embodiment. As illustrated in FIG. 20, the force sensor 1C includes the displacement sensor 20 and a first frame 30c. The displacement sensor 20 has the same structure as that described in the first embodiment. The same numerals as those of the first embodiment are thus labeled and the descriptions thereof are omitted.

The first frame 30c includes a ceiling 110 having a first opposed surface 110a arranged to face the light-emitting unit 21 on the optical axis of the light-emitting unit 21. On the first opposed surface 110a, a mirror 111 serving as a reflector is provided.

The first frame 30c further includes legs 112 to 115 that support the first opposed surface 110a from four directions and are deformed in a manner capable of displacing diffuse light reflected by the mirror 111 only in both of the first direction (in this case, in the X-axis direction) and the second direction (in this case, in the Y-axis direction).

The legs 112 and 113 are provided on both sides of the first opposed surface 110a in the first direction, and a lower end portion 112a of the leg 112 and a lower end portion 113a of the leg 113 are fixed to a mounting surface on which the displacement sensor 20 is mounted. The legs 114 and 115 are provided on both sides of the first opposed surface 110a in the second direction, and a lower end portion 114a of the leg 114 and a lower end portion 115a of the leg 115 are fixed to the mounting surface on which the displacement sensor 20 is mounted.

As described above, the force sensor 1C according to the fifth embodiment includes the first frame 30c that supports the first opposed surface 110a provided with the mirror 111 such that the first opposed surface 110a faces the displacement sensor 20 by the four deformable legs 112 to 115. The force sensor 1C thus structured can also detect shearing forces in two directions perpendicular to each other.

Figure 21:
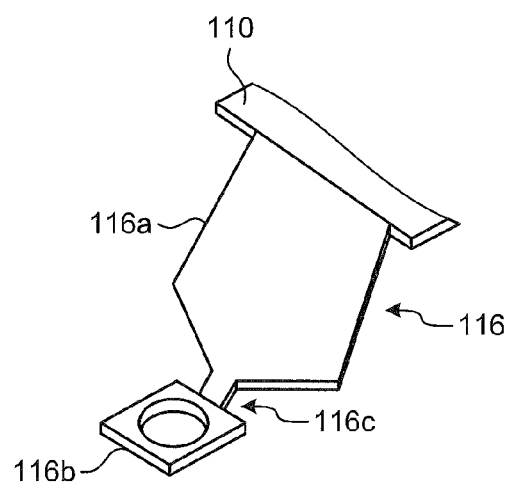
FIG. 21 is an explanatory view illustrating a modification of legs of the force sensor according to the fifth embodiment.

Changing the shapes of the four legs 112 to 115 can increase the shearing force detection sensitivity of the force sensor 1C. FIG. 21 is an explanatory view illustrating a modification of the legs of the force sensor 1C according to the fifth embodiment. FIG. 21 illustrates one of the four legs.

As illustrated in FIG. 21, a leg 116 of the force sensor 1C according to the modification includes a leg body 116a extending from the ceiling 110 of the first frame 30c, a lower end portion 116b fixed to the mounting surface, and a linking portion 116c provided between the leg body 116a and the lower end portion 116a. The width of the linking portion 116b is smaller than those of the leg body 116a and the lower end portion 116b.

As described above, a linking portion 116c the width of which is smaller than those of the leg body 116a and the lower end portion 116b is provided between the leg body 116a and the lower end portion 116b. This structure causes the linking portion 116c to be deformed even when a smaller shearing force is applied to the ceiling 110. The structure including the leg 116 thus can further increase the shearing force detection sensitivity of the force sensor 1C.

Other Embodiments

In the embodiments described above, the variable frame is formed in an approximate trapezoidal shape in a side view, and when shearing force is applied to the variable frame, the ceiling of the variable frame is inclined, thereby causing the irradiation area R of the reflected diffuse laser light to be displaced (refer to FIGS. 4A and 4B).

The method for displacing the irradiation area R in accordance with shearing force is not limited to the method described above. For example, the use of a mirror having a convex or concave reflection surface can achieve the displacement of the irradiation area R even when the variable frame is formed in an approximate rectangular shape in a side view, in other words, even when a structure is adopted in which the ceiling of the variable frame is not inclined. Specifically, when the variable frame is formed in an approximate rectangular shape in a side view and shearing force is applied to the variable frame, the ceiling of the variable frame is not inclined because the ceiling of the variable frame is moved while being kept horizontal, but the reflection angle of diffuse laser light is changed due to the change in position of the mirror, thereby making it possible to displace the irradiation area R.

In the embodiments described above, the displacement sensor includes the light-emitting unit, that is, the displacement sensor and the light-emitting unit are integrated. The displacement sensor and the light-emitting unit may be separated.

The force sensor according to the first embodiment can detect torque as described above. The force sensors according to the second to the fifth embodiments can also detect torque. The force sensors according to the second to the fifth embodiments each can detect torque applied to any rotating body by being provided between the rotating body and a member that applies torque causing the rotating body to rotate.

Figure 22:
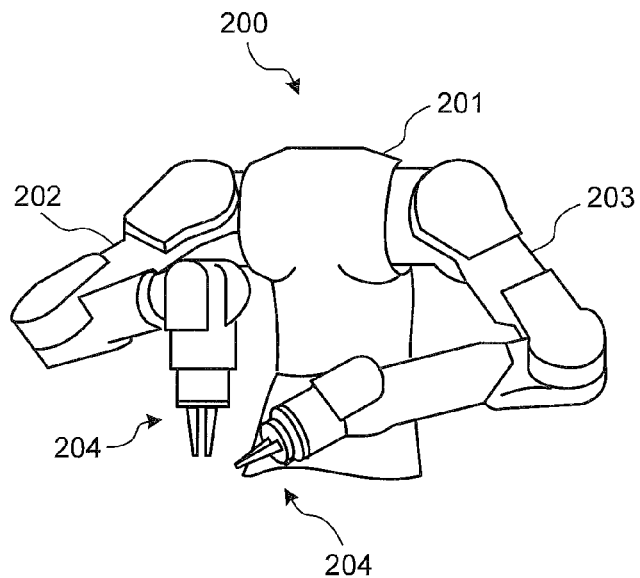
FIG. 22 is an explanatory view illustrating a robot having the force sensors according to the first embodiment.
Figure 23:
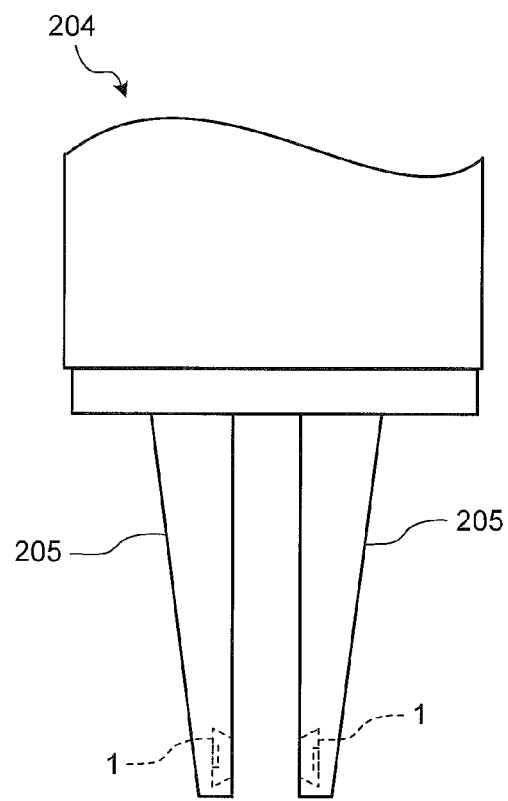
FIG. 23 is an explanatory view illustrating an end effector of the robot having the force sensors according to the first embodiment.

The respective force sensors according to the embodiments described above are provided to a robot, for example. FIG. 22 is an explanatory view illustrating a robot having the force sensors according to the first embodiment. FIG. 23 is an explanatory view illustrating an end effector of the robot having the force sensors according to the first embodiment.

As illustrated in FIG. 22, a robot 200 having the force sensors according to the first embodiment includes a body 201, a right arm 202 and a left arm 203 extending from the respective shoulder portions of the body 201, and end effectors 204 provided to the respective end portions of the right arm 202 and the left arm 203. Each of the right arm 202 and the left arm 203 is a robot arm having six axes of freedom.

As illustrated in FIG. 23, the end effector 204 is a robot hand having a pair of gripping claws 205 that grip a work to be processed. The force sensors 1 according to the first embodiment are provided on the opposed surfaces of the end portions of the gripping claws 205, that is, on the surfaces that come into contact with the work when the gripping claws 205 grip the work.

The force sensor 1 is buried in each gripping claw 205 such that the ceiling 32 (refer to FIG. 1) and the gripping surface of the gripping claw 205 are on the same plane and the ceiling 32 is exposed from the gripping surface. The ceiling 32 of the force sensor 1 may be covered with an elastic cover.

The robot 200 can detect shearing force acting on the gripping claws 205 when gripping a work, thereby making it possible to reduce a damage to the work caused by an excessive shearing force by performing the griping operation while monitoring the detected shearing force.

The robot 200 is exemplified that has two arms of the right arm 202 and the left arm 203. The robot provided with the force sensors 1 may be a robot having a single arm. The number of gripping claws 205 of the end effector 204 is not limited to two. The force sensors 1 included in the robot 200 are not limited to those of the first embodiment. Any of the force sensors according to the respective embodiments may be applicable.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A force sensor, comprising:
a light-emitting unit that emits diffuse light;
a pair of first light detectors that are arranged facing in a first direction with the light-emitting unit interposed between the first light detectors;
a reflector that is arranged to face the light-emitting unit on an optical axis of the light-emitting unit, the reflector reflecting the diffuse light emitted from the light-emitting unit toward the pair of first light detectors;
a first frame that is deformed in the first direction so that a reflection range of the diffuse light reflected by the reflector mounted on the first frame is displaced in the first direction;
a pair of second light detectors that are arranged in a second direction perpendicular to the first direction with the light-emitting unit interposed therebetween; and
a second frame that is deformed in the second direction so that the reflection range of the diffuse light reflected by the reflector is displaced in the second direction, wherein
the first frame includes:
a first leg part that is fixed to a mounting surface on which the light-emitting unit is mounted; and
a first opposed surface that is supported by the first leg part so that the first opposed surface faces the light-emitting unit on the optical axis of the light-emitting unit, the first opposed surface having an opening provided in an area including a position intersecting with the optical axis of the light-emitting unit,
the second frame includes:
a second leg part that is connected to the first frame; and
a second opposed surface that is supported by the second leg part so that the second opposed surface faces the light-emitting unit on the optical axis of the light-emitting unit, the opening of the first opposed surface being located between the second opposed surface and the light-emitting unit, and the reflector is provided, on the second opposed surface, in the area including the position intersecting with the optical axis of the light-emitting unit.

2. The force sensor according to claim 1, wherein
the first leg part includes two legs,
the second leg part includes two legs,
the two legs of the first leg part of the first frame are provided on both sides of the first opposed surface in the first direction,
the first frame further includes connecting arms that are provided on both sides of the first opposed surface in the second direction,
the two legs of the second leg part of the second frame are provided on both sides of the second opposed surface in the second direction, and
the two legs of the second leg part are respectively connected to the connecting arms of the first frame on sides closer to the mounting surface of the light-emitting unit than to the first opposed surface.

3. The force sensor according to claim 1, wherein
the first frame includes a connecting portion at which the first leg part and the first opposed surface are connected at an angle other than a right angle, and
the connecting portion is deformed in the first direction so that the reflection range of the diffuse light reflected by the reflector is displaced in the first direction.

4. The force sensor according to claim 2, wherein
the first frame includes connecting portions at which the two legs of the first leg part and the first opposed surface are respectively connected at an angle other than a right angle, and
the connecting portions are deformed in the first direction so that the reflection range of the diffuse light reflected by the reflector is displaced in the first direction.

5. The force sensor according to claim 1, wherein
the second frame includes a connecting portion at which the second leg part and the second opposed surface are connected at an angle other than a right angle, and
the connecting portion is deformed in the second direction so that the reflection range of the diffuse light reflected by the reflector is displaced in the second direction.

6. The force sensor according to claim 2, wherein
the second frame includes connecting portions at which the two legs of the second leg part and the second opposed surface are respectively connected at an angle other than a right angle, and
the connecting portions are deformed in the second direction so that the reflection range of the diffuse light reflected by the reflector is displaced in the second direction.

7. The force sensor according to claim 3, wherein
the second frame includes a connecting portion at which the second leg part and the second opposed surface are connected at an angle other than the right angle, and
the connecting portion is deformed in the second direction so that the reflection range of the diffuse light reflected by the reflector is displaced in the second direction.

8. A force sensor, comprising:
a light-emitting unit that emits diffuse light;
a pair of first light detectors that are arranged facing in a first direction with the light-emitting unit interposed between the first light detectors;

a first frame that includes an opposed surface facing the light-emitting unit on an optical axis of the light-emitting unit and is fixed to a mounting surface on which the light-emitting unit is mounted, the first frame having one degree of freedom in an arrangement direction of the pair of light-emitting units;
a reflector that is provided on the opposed surface of the first frame, the reflector reflecting the diffuse light emitted from the light-emitting unit toward the pair of light-emitting units;
a pair of second light detectors that are arranged in a second direction perpendicular to the first direction with the light-emitting unit interposed therebetween; and
a second frame that is deformed in the second direction so that the reflection range of the diffuse light reflected by the reflector is displaced in the second direction, wherein
the first frame includes:
a first leg part that is fixed to a mounting surface on which the light-emitting unit is mounted; and
a first opposed surface that is supported by the first leg part so that the first opposed surface faces the light-emitting unit on the optical axis of the light-emitting unit, the first opposed surface having an opening provided in an area including a position intersecting with the optical axis of the light-emitting unit,
the second frame includes:
a second leg part that is connected to the first frame; and
a second opposed surface that is supported by the second leg part so that the second opposed surface faces the light-emitting unit on the optical axis of the light-emitting unit, the opening of the first opposed surface being located between the second opposed surface and the light-emitting unit, and
the reflector is provided, on the second opposed surface, in the area including the position intersecting with the optical axis of the light-emitting unit.

9. A force sensor, comprising:
a light-emitting unit that emits diffuse light;
a pair of first light detectors that are arranged facing in a first direction with the light-emitting unit interposed between the first light detectors;
a reflector that is arranged to face the light-emitting unit on an optical axis of the light-emitting unit, the reflector reflecting the diffuse light emitted from the light-emitting unit toward the pair of first light detectors;
a first frame that includes an opposed surface provided to face the light-emitting unit on the optical axis of the light-emitting unit and is fixed to a mounting surface on which the light-emitting unit is mounted, the first frame being deformed in the first direction so that a reflection range of the diffuse light reflected by the reflector is displaced in the first direction;
a pair of second light detectors that are arranged in a second direction perpendicular to the first direction with the light-emitting unit interposed therebetween; and
a second frame that is deformed in the second direction so that the reflection range of the diffuse light reflected by the reflector is displaced in the second direction, wherein
the first frame includes:
a first leg part that is fixed to a mounting surface on which the light-emitting unit is mounted; and a first opposed surface that is supported by the first leg part so that the first opposed surface faces the light-emitting unit on the optical axis of the light-emitting unit, the first opposed surface having an opening provided in an area including a position intersecting with the optical axis of the light-emitting unit, the second frame includes:
a second leg part that is connected to the first frame; and
a second opposed surface that is supported by the second leg part so that the second opposed surface faces the light-emitting unit on the optical axis of the light-emitting unit, the opening of the first opposed surface being located between the second opposed surface and the light-emitting unit, the reflector is provided, on the second opposed surface, in the area including the position intersecting with the optical axis of the light-emitting unit, and the reflector is provided on the opposed surface of the first frame.

10. A robot comprising:
an end effector; and
a force sensor that is provided in the end effector,
the force sensor comprising:
a light-emitting unit that emits diffuse light;
a pair of first light detectors that are arranged facing in a first direction with the light-emitting unit interposed between the first light detectors;
a reflector that is arranged to face the light-emitting unit on an optical axis of the light-emitting unit, the reflector reflecting the diffuse light emitted from the light-emitting unit toward the pair of first light detectors;
a first frame that is deformed in the first direction so that a reflection range of the diffuse light reflected by the reflector mounted on the first frame is displaced in the first direction;
a pair of second light detectors that are arranged in a second direction perpendicular to the first direction with the light-emitting unit interposed therebetween; and
a second frame that is deformed in the second direction so that the reflection range of the diffuse light reflected by the reflector is displaced in the second direction, wherein
the first frame includes:
a first leg part that is fixed to a mounting surface on which the light-emitting unit is mounted; and
a first opposed surface that is supported by the first leg part so that the first opposed surface faces the light-emitting unit on the optical axis of the light-emitting unit, the first opposed surface having an opening provided in an area including a position intersecting with the optical axis of the light-emitting unit, the second frame includes:
a second leg part that is connected to the first frame; and
a second opposed surface that is supported by the second leg part so that the second opposed surface faces the light-emitting unit on the optical axis of the light-emitting unit, the opening of the first opposed surface being located between the second opposed surface and the light-emitting unit, and the reflector is provided, on the second opposed surface, in the area including the position intersecting with the optical axis of the light-emitting unit.

11. A force sensor, comprising:
means for emitting diffuse light;
means for reflecting the diffuse light emitted from the means for emitting, the means for reflecting being arranged to face the means for emitting on an optical axis of the means for emitting;
a pair of first light detectors that detect the diffuse light reflected by the means for reflecting, the first light detectors being arranged facing in one direction with the means for emitting interposed between the first light detectors;
means for displacing a reflection range of the diffuse light reflected by the means for reflecting in the one direction by an external force, the means for displacing including a first frame;
a pair of second light detectors that are arranged in a second direction perpendicular to the first direction with the means for emitting interposed therebetween; and
a second frame that is deformed in the second direction so that the reflection range of the diffuse light reflected by the means for reflecting is displaced in the second direction, wherein
the first frame includes:
a first leg part that is fixed to a mounting surface on which the means for emitting is mounted; and
a first opposed surface that is supported by the first leg part so that the first opposed surface faces the means for emitting on the optical axis of the means for emitting, the first opposed surface having an opening provided in an area including a position intersecting with the optical axis of the means for emitting,
the second frame includes:
a second leg part that is connected to the first frame; and
a second opposed surface that is supported by the second leg part so that the second opposed surface faces the means for emitting on the optical axis of the means for emitting, the opening of the first opposed surface being located between the second opposed surface and the means for emitting, and
the means for reflecting is provided, on the second opposed surface, in the area including the position intersecting with the optical axis of the means for emitting.

* * * * *